US009554774B2

(12) United States Patent
Moore et al.

(10) Patent No.: US 9,554,774 B2
(45) Date of Patent: Jan. 31, 2017

(54) SYSTEM AND CATHETER FOR IMAGE GUIDANCE AND METHODS THEREOF

(75) Inventors: Thomas C. Moore, Livermore, CA (US); Kendall R. Waters, Livermore, CA (US); Stephanie J. Buech, Redwood City, CA (US); Robert Zelenka, Milpitas, CA (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 629 days.

(21) Appl. No.: 12/633,278

(22) Filed: Dec. 8, 2009

(65) Prior Publication Data
US 2010/0152590 A1 Jun. 17, 2010

Related U.S. Application Data

(60) Provisional application No. 61/120,762, filed on Dec. 8, 2008, provisional application No. 61/158,075, filed on Mar. 6, 2009.

(51) Int. Cl.
*A61B 6/00* (2006.01)
*A61B 8/00* (2006.01)
(Continued)

(52) U.S. Cl.
CPC ........... *A61B 8/4461* (2013.01); *A61B 8/0841* (2013.01); *A61B 8/12* (2013.01); *A61B 8/445* (2013.01);
(Continued)

(58) Field of Classification Search
USPC ......................................................... 600/435
See application file for complete search history.

(56) References Cited

U.S. PATENT DOCUMENTS 5,244,461 A * 9/1993 Derlien ........................ 604/65
5,321,106 A 6/1994 LaPointe
(Continued)

FOREIGN PATENT DOCUMENTS

EP 1929954 A1 6/2008
EP 2358278 A2 8/2011
(Continued)

OTHER PUBLICATIONS

International Search Report for International Application No. PCT/US2009/067094, dated Jul. 20, 2010.
(Continued)

*Primary Examiner* — Amanda Lauritzen Moher
*Assistant Examiner* — Shahdeep Mohammed
(74) *Attorney, Agent, or Firm* — Fredrikson & Byron, P.A.

(57) ABSTRACT

A catheter-based imaging system includes a catheter having a telescoping proximal end, a distal end having a distal sheath and a distal lumen, a working lumen, and an ultrasonic imaging core. The ultrasonic imaging core is arranged for rotation and linear translation. The system further includes a patient interface module including a catheter interface, a rotational motion control system that imparts controlled rotation to the ultrasonic imaging core, a linear translation control system that imparts controlled linear translation to the ultrasonic imaging core, and an ultrasonic energy generator and receiver coupled to the ultrasonic imaging core. The system further includes an image generator coupled to the ultrasonic energy receiver that generates an image.

27 Claims, 28 Drawing Sheets

(51) Int. Cl.
    *A61B 8/12*     (2006.01)
    *A61B 8/08*     (2006.01)
    *A61B 18/14*     (2006.01)
    *A61B 1/018*     (2006.01)
    *A61B 17/00*     (2006.01)

(52) U.S. Cl.
    CPC ......... *A61B 8/5223* (2013.01); *A61B 18/1492* (2013.01); *A61B 34/25* (2016.02); *A61B 90/37* (2016.02); *A61B 1/018* (2013.01); *A61B 8/5253* (2013.01); *A61B 2017/00243* (2013.01); *A61B 2017/00557* (2013.01); *A61B 2090/3784* (2016.02)

(56) References Cited

U.S. PATENT DOCUMENTS

| | | | | |
|---|---|---|---|---|
| 5,327,885 | A | * | 7/1994 | Griffith .................. 600/470 |
| 5,361,768 | A | * | 11/1994 | Webler et al. ............ 600/445 |
| 5,827,313 | A | | 10/1998 | Ream .................... 606/171 |
| 5,908,395 | A | * | 6/1999 | Stalker et al. ............ 600/585 |
| 6,004,269 | A | * | 12/1999 | Crowley et al. ........... 600/439 |
| 6,004,271 | A | * | 12/1999 | Moore .................... 600/445 |
| 6,251,078 | B1 | | 6/2001 | Moore et al. |
| 6,292,681 | B1 | | 9/2001 | Moore |
| 6,319,227 | B1 | | 11/2001 | Mansouri-Ruiz |
| 6,398,755 | B1 | | 6/2002 | Belef et al. |
| 6,511,432 | B2 | | 1/2003 | Moore et al. |
| 6,592,520 | B1 | | 7/2003 | Peszynski et al. |
| 6,974,465 | B2 | | 12/2005 | Belef et al. |
| 8,157,741 | B2 | | 4/2012 | Hirota |
| 8,298,156 | B2 | | 10/2012 | Manstrom et al. |
| 2001/0021841 | A1 | | 9/2001 | Webler et al. |
| 2001/0045935 | A1 | | 11/2001 | Chang et al. |
| 2001/0047165 | A1 | | 11/2001 | Makower et al. |
| 2002/0047367 | A1 | * | 4/2002 | Kim ............ H02K 33/02 310/80 |
| 2002/0050169 | A1 | * | 5/2002 | Ritter et al. ................. 73/606 |
| 2002/0107447 | A1 | * | 8/2002 | Suorsa et al. .............. 600/466 |
| 2002/0183723 | A1 | * | 12/2002 | Belef et al. ................... 606/1 |
| 2003/0013958 | A1 | | 1/2003 | Govari et al. |
| 2003/0135995 | A1 | | 7/2003 | Glasson |
| 2003/0187369 | A1 | | 10/2003 | Lewis et al. |
| 2004/0078036 | A1 | | 4/2004 | Keidar |
| 2004/0147920 | A1 | | 7/2004 | Keidar |
| 2004/0215130 | A1 | * | 10/2004 | Rioux et al. ................. 604/35 |
| 2006/0122514 | A1 | | 6/2006 | Byrd et al. |
| 2006/0241445 | A1 | | 10/2006 | Altmann et al. |
| 2006/0241469 | A1 | | 10/2006 | Rold et al. |
| 2006/0241484 | A1 | | 10/2006 | Horiike et al. |
| 2006/0287599 | A1 | * | 12/2006 | Cimino ................... 600/471 |
| 2007/0093752 | A1 | * | 4/2007 | Zhao et al. ............... 604/131 |
| 2007/0106147 | A1 | | 5/2007 | Altmann et al. |
| 2007/0167752 | A1 | * | 7/2007 | Proulx et al. .............. 600/437 |
| 2007/0167821 | A1 | | 7/2007 | Lee et al. |
| 2008/0195041 | A1 | * | 8/2008 | Goldfarb et al. ......... 604/96.01 |
| 2008/0255449 | A1 | | 10/2008 | Warnking et al. |
| 2009/0054776 | A1 | * | 2/2009 | Sasaki .................... 600/443 |
| 2009/0069693 | A1 | * | 3/2009 | Burcher et al. ........... 600/459 |
| 2009/0124998 | A1 | * | 5/2009 | Rioux et al. .............. 604/506 |
| 2009/0156941 | A1 | | 6/2009 | Moore |
| 2009/0234302 | A1 | * | 9/2009 | Hoendervoogt et al. ..................... 604/288.01 |
| 2010/0057019 | A1 | | 3/2010 | Zalenka |
| 2010/0152590 | A1 | | 6/2010 | Moore et al. |
| 2010/0179434 | A1 | | 7/2010 | Thornton |
| 2010/0249603 | A1 | | 9/2010 | Hastings et al. |
| 2013/0137963 | A1 | | 5/2013 | Olson |
| 2014/0343433 | A1 | | 11/2014 | Elbert |
| 2015/0182190 | A1 | | 7/2015 | Hiltner et al. |

FOREIGN PATENT DOCUMENTS

| | | |
|---|---|---|
| JP | 63122923 | 5/1988 |
| JP | 63302836 | 9/1988 |
| JP | 04-017843 | 1/1992 |
| JP | 05-244694 | 9/1993 |
| JP | 07-008497 | 1/1995 |
| JP | 07-095980 | 4/1995 |
| JP | H07136171 A | 5/1995 |
| JP | 07-184902 | 7/1995 |
| JP | 7-508204 | 9/1995 |
| JP | 08-112286 | 5/1996 |
| JP | H08112286 A | 5/1996 |
| JP | 63-281632 | 11/1998 |
| JP | 2000157546 | 6/2000 |
| JP | 2002301070 A | 10/2002 |
| JP | 2003-265483 A | 9/2003 |
| JP | 2004209277 A | 7/2004 |
| JP | 2005507273 | 3/2005 |
| JP | 2005536289 A | 12/2005 |
| JP | 2006-102240 | 4/2006 |
| JP | 2007-105450 | 4/2007 |
| JP | 2007-152094 | 6/2007 |
| JP | 2007-268132 | 10/2007 |
| JP | 2008155022 A | 7/2008 |
| JP | 2008178676 A | 8/2008 |
| JP | 2008053887 | 11/2008 |
| JP | 2008277834 | 11/2008 |
| JP | 2008539887 A | 11/2008 |
| JP | 2012510885 A | 5/2012 |
| WO | 9203095 A1 | 3/1992 |
| WO | 03/011139 A1 | 2/2003 |
| WO | 2008042423 A2 | 4/2008 |
| WO | 2008086613 A1 | 7/2008 |
| WO | 2010077632 A2 | 7/2010 |
| WO | 2010107916 A1 | 9/2010 |

OTHER PUBLICATIONS

Supplementary European Search Report of European Pat. App. No. 09836694, May 19, 2015, 8 pages, European Patent Office, Munich, Germany.

Japanese Patent Application No. 2015-151658, Notice of Reasons for Refusal dated Jul. 28, 2016, 6 pages (including 3 pages English Machine Translation).

Japanese Patent Application No. 2015-151658, Search Report dated Jul. 25, 2016, 30 pages (including 13 pages English Machine Translation).

\* cited by examiner

# SYSTEM AND CATHETER FOR IMAGE GUIDANCE AND METHODS THEREOF

PRIORITY CLAIM

The present application claims the benefit of U.S. Provisional Patent Application Ser. No. 61/120,762, filed Dec. 8, 2008, and U.S. Provisional Patent Application Ser. No. 61/158,075, filed Mar. 6, 2009, which applications are incorporated herein by reference in their entirety.

BACKGROUND

The present invention generally relates to ultrasound imaging catheters. The present invention further relates to transesophageal echocardiographic catheters for the purpose of guiding cardiac interventions. The present invention still further relates further to intracardiac echocardiographic catheters for the purpose of guiding cardiac interventions.

Atrial fibrillation (AF) is the most common arrhythmia in the United States and other developed countries. Nearly two (2) million individuals in the United States have AF. Catheter ablation is increasingly selected therapy for AF. Radiofrequency ablation is the most common form of AF ablation.

AF ablation procedures are however not without serious risks. Such risks include the formation of atrio-esophageal fistulas and thrombus. Successful outcome of RF ablation procedures depends in part on the contiguity and transmurality of the ablative lesions and is largely dependent on the skill of the operator.

Image guidance techniques such as fluoroscopy, electroanatomic mapping (EAM), and echocardiography facilitate such procedures. These existing technologies however have important limitations. Fluoroscopy provides a two-dimensional view of external structures, has poor soft tissue contrast, requires the injection of contrast, and exposes the patient and staff to radiation. EAM is useful for mapping the electrical properties of the left atrial wall and pulmonary veins in order to determine the location of the susceptible substrates and focal triggers that support AF. EAM is often combined with catheter tracking technologies to facilitate catheter positioning. However, EAM is time consuming, complex, and does not provide real-time imaging of cardiac tissue. Further, registration can be lost due to cardiac motion. Intracardiac echocardiography (ICE) is the most commonly used ultrasound-based technique for AF ablation image guidance. However, ICE catheters are practically limited to imaging from the right atrium due to their relatively large size. This leads to relatively poor image performance, particularly for key cardiac structures such as the left pulmonary veins. Transesophageal echocardiography (TEE) enables imaging of the left atrium from the esophagus. However, relatively poor near-field resolution of current TEE probes makes imaging of important cardiac structures difficult, such as the left atrium posterior wall. Further, TEE often requires general anesthesia due to patient discomfort from large probe size.

In view of the limitations to image guidance technologies for AF ablation noted heretofore, there is a need in the art for real-time visualization of the left atrium posterior wall and pulmonary veins, pre-intervention mapping of susceptible substrates, ablation lesion assessment, and the ability to mitigate complications.

SUMMARY OF THE INVENTION

According to one embodiment, a catheter-based imaging system, comprises a catheter having a telescoping proximal end, a distal end having a distal sheath and a distal lumen, a working lumen, and an ultrasonic imaging core. The ultrasonic imaging core is arranged for rotation and linear translation. The system further includes a patient interface module including a catheter interface, a rotational motion control system that imparts controlled rotation to the ultrasonic imaging core, a linear translation control system that imparts controlled linear translation to the ultrasonic imaging core, and an ultrasonic energy generator and receiver coupled to the ultrasonic imaging core. The system further comprises an image generator coupled to the ultrasonic energy receiver that generates an image.

The catheter may be adapted for intracardiac use or transesophageal use. The catheter-based imaging system may further comprise a compliant balloon at the catheter distal end. The catheter may comprise an inflation lumen in fluid communication with the balloon. The catheter may comprise a deflation lumen in fluid communication with the balloon. The catheter distal end may be in fluid communication with the balloon. The catheter may also be dimensioned for transnasal delivery.

The ultrasonic imaging core may comprise at least one transducer. The ultrasonic imaging core may comprise at least one transducer array. The linear translation control system may comprise an ultrasonic piezoelectric motor. The linear translation system may comprise a gear and linkage arm. The patient interface module may comprise a linear translation position sensor.

The catheter-based imaging system may further comprise an identifier that provides identification of susceptible substrates responsive to ultrasound tissue classifiers. The catheter-based imaging system may further comprise a temperature monitor that monitors luminal esophageal temperature responsive to ultrasound tissue classifiers. The catheter-based imaging system may further comprise a titrator that maps contiguity and transmurality of ablative lesions responsive to ultrasound tissue classifiers. The catheter-based imaging system may further comprise a stage that stitches scanned image sub-volumes into a large scanned image volume.

The catheter-based imaging system may further comprise a stage responsive to the ultrasonic imaging core for providing synthetic aperture imaging. The catheter-based imaging system may further comprise a stage responsive to the at least one transducer array for providing synthetic aperture imaging.

The catheter-based imaging system may further comprise a stage responsive to the ultrasonic imaging core for providing synthetic aperture beam steering. The catheter-based imaging system may further comprise a stage responsive to the at least one transducer array for providing synthetic aperture beam steering. The catheter distal end may comprise a septum, an atraumatic tip, and a septum puncture port.

The catheter distal tip may comprise a short monorail guidewire receiver. The catheter may comprise an over-the-wire guidewire receiver. The catheter may comprise a steerable section. The catheter may comprise a second working lumen.

The ultrasonic imaging core comprises a magnetic tracking sensor. The catheter distal sheath may comprise a radio-opaque marker band.

The linear translation control system may be arranged to impart continuous controlled translation to the ultrasonic imaging core. The linear translation control system may be arranged to impart controlled bidirectional translation to the ultrasonic imaging core.

BRIEF DESCRIPTION OF THE DRAWINGS

The features of the present invention which are believed to be novel are set forth with particularity in the appended claims. The invention, together with further features and advantages thereof, may best be understood by making reference to the following descriptions taken in conjunction with the accompanying drawings, in the several figures of which like reference numerals identify identical elements, and wherein:

DETAILED DESCRIPTION OF THE EMBODIMENTS

Figure 1:
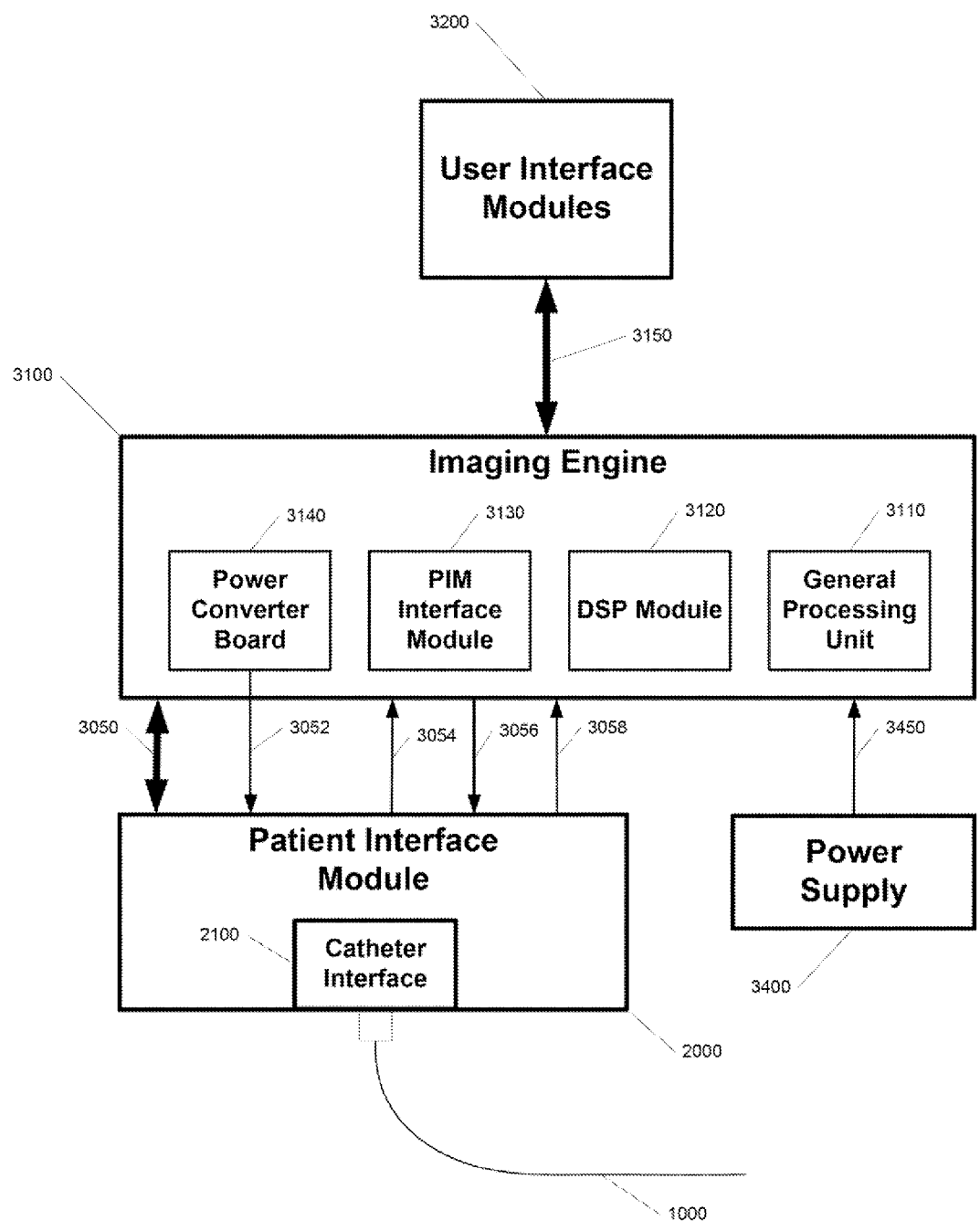
FIG. 1 is a high-level diagram of a catheter-based imaging system of a type which may incorporate various embodiments of the invention to advantage.

FIG. 1 shows a high-level diagram of an echocardiographic system and catheter. The system comprises an imaging engine 3100 and a patient interface module (PIM) 2000. The imaging engine 3100 is the central component of the system and performs all image generation, display, and control of the system components. The imaging engine 3100 comprises a general processing unit 3110, a digital signal processing (DSP) module 3120, and a PIM interface module 3130. The PIM 2000 is in mechanical and electrical communication with an echocardiographic catheter 1000.

A catheter is a common medical device comprising a flexible tubular body having a proximal end and a distal end. A catheter configured in accordance with an embodiment of the present invention may comprise an outer tube having a proximal end, an inner sheath slidingly received within the outer tube and extending distally from the outer tube, and a rotatable shaft (or drive cable) extending from the proximal end of the outer tube to within the inner sheath. The rotatable shaft is axially fixed with respect to the outer tube and is axially moveable within and with respect to the inner sheath. An embodiment of the proximal section of such a catheter including a telescoping section is described in additional detail in, for example, U.S. patent application Ser. No. 12/336,441 the complete disclosure of which is hereby incorporated herein by reference.

Figure 2:
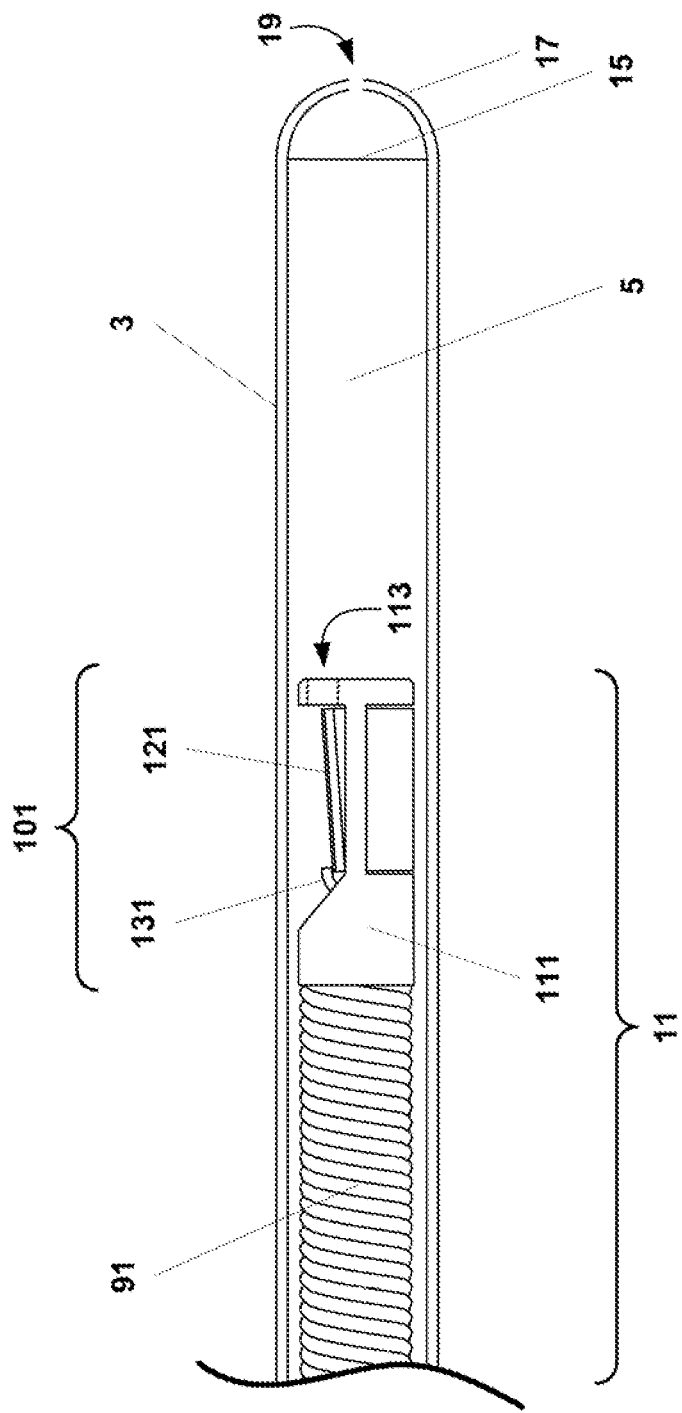
FIG. 2 is a side view in partial cross section of the distal section of an echocardiography catheter according to an embodiment of the invention.

FIG. 2 shows a distal section of a catheter comprising a distal shaft 3 having an imaging lumen 5 wherein an ultrasound imaging core 11 is positioned. The distal section is generally formed by extrusion of thermoplastics such as polyethylene or nylon. The distal shaft may also be formed of more than one layer of thermoplastics. The distal section further comprises a septum 15, an atraumatic distal tip 17, and a septum puncture port 19. The septum 15 may be comprised of a polymer material such as a room-temperature vulcanizing (RTV) silicone. A syringe needle (not shown) is inserted through the septum puncture port 19 and punctures the septum 15 to fill the distal sheath lumen 5 with an ultrasonically transparent fluid such as a sterile saline solution. Upon withdrawal of the syringe needle the septum 15 seals itself. The use of a self-sealing septum prevents the pulling of fluids, such as blood or air, into the distal sheath as the imaging core 11 translates towards the proximal end.

The imaging core 11 comprises a drive cable 91 attached to a distal housing assembly 101. The distal housing assembly 101 comprises a distal housing 111, a transducer 121, and a transmission line 131. Such a distal housing 111 further comprises a distal opening 113 that facilitates fluid flow across the face of the transducer stack 121. The distal housing is described in additional detail in U.S. patent application Ser. No. 12/330,308 the complete disclosure of which is hereby incorporated herein by reference.

The distal shaft 3 comprises an elongated tube having at least one layer. The distal shaft can be tapered or straight. For example, the distal shaft may be a straight tube having an outer diameter in the range of 0.080" to 0.350" for intracardiac and transesophageal catheters. The outer diameter may be more generally 10 Fr (0.131") or smaller for intracardiac catheters. Intracardiac catheters having profiles 8 Fr (0.105") or smaller may be more acceptable to deliver via a transseptal route to the left atrium wherein imaging performance may be better for AF ablation guidance than from the right atrium. The outer diameter may be more generally between 12 Fr (0.158") and 25 Fr (0.328") for transesophageal catheters that can be delivered transnasally.

The drive cable 91 generally comprises at least one single or multi-filar stainless steel or similar material round, square or flat wire coil with an outer diameter generally in the range 0.10 mm to 3.50 mm. The elongation and compression of the drive cable 91 during acceleration must be minimized to insure accurate positioning. The drive cable 91 should also minimize non-uniform rotation of the imaging core 11.

The transducer stack 121 operates over frequency ranges of 5 MHz to 60 MHz, generally between 5 MHz and 20 MHz for intracardiac and transesophageal imaging. The transducer stack 121 comprises at least a piezoelectric layer. The transducer stack 121 generally further comprises conductive layers, at least one matching layer, and a backing layer. Transducer stacks for imaging catheters are known to those skilled in the art. An exemplary transducer for an 8 Fr sized catheter has an aperture of approximately 1.6 mm by 2.4 mm and has a focal length between 1 cm and 4 cm, generally between 2 cm and 3 cm. Methods to focus transducers are known to those skilled in the art of transducer fabrication. A transmission line 131 electrically connects the transducer stack 121 to transceiver electronics housed in the patient interface module.

Figure 3:
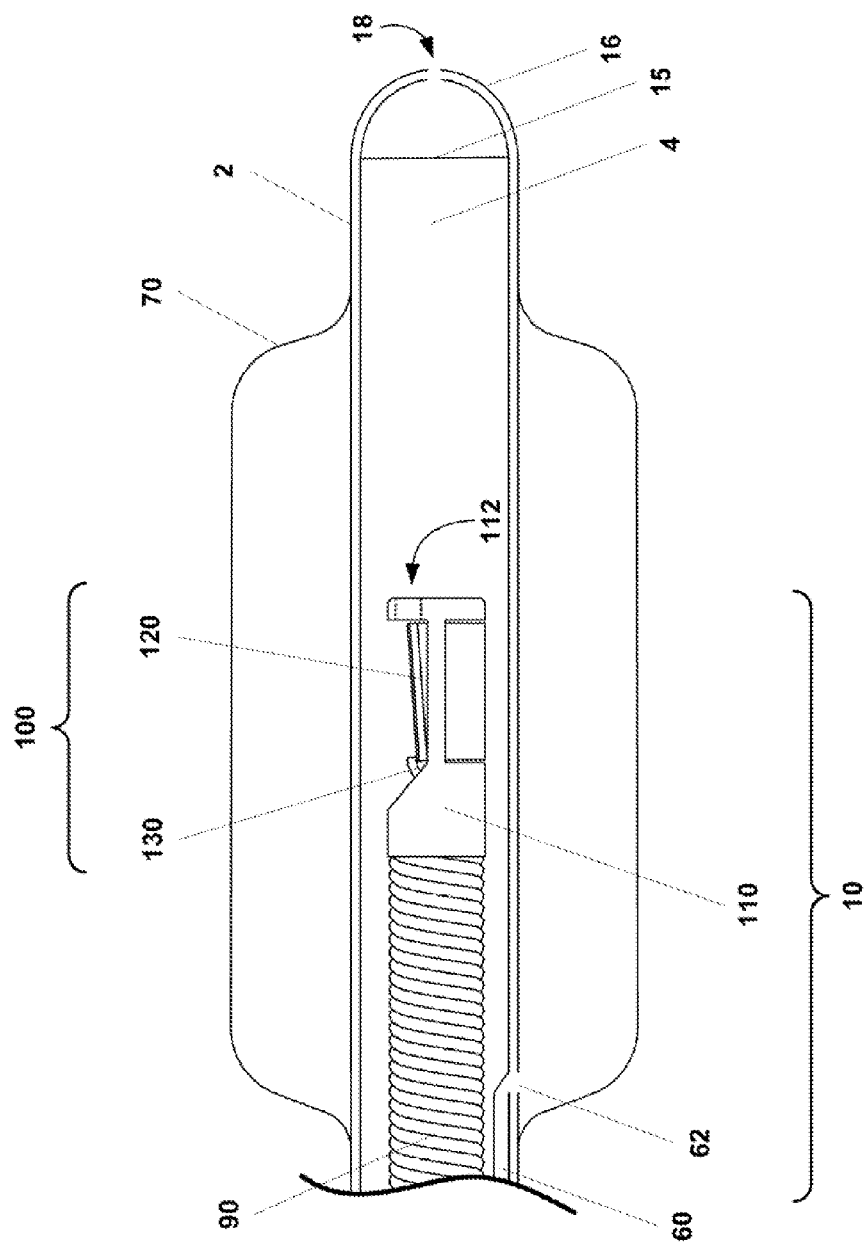
FIG. 3 is a side view in partial cross section of the distal section of a transesophageal echocardiography balloon catheter according to an embodiment of the invention.

Referring now to FIGS. 3-6, several embodiments of the distal section of transesophageal echocardiographic catheters are illustrated. FIG. 3 shows a side view of an embodiment of the distal section of the catheter comprising a balloon envelope 70, an inflation lumen 60, an inflation port 62, and an ultrasonic imaging core 10. The ultrasonic imaging core 10 comprises a drive cable 90 and a distal housing assembly 100 further comprising a distal housing 110, a transducer stack 120, and a transmission line 130. The distal housing 110 further comprises a distal opening 112 that facilitates fluid flow across the face of the transducer stack. The transducer stack 120 can be focused or unfocused. An exemplary transducer for a 15 Fr sized catheter has a circular aperture of up to approximately 4.2 mm and has a focal length between 1 cm and 4 cm, generally between 2 cm and 3 cm. Methods to focus transducers are known to those skilled in the art of transducer fabrication.

The distal section of the balloon imaging catheter further comprises a sheath 2, a distal sheath lumen 4, a septum 15, an atraumatic distal tip 16, and a septum puncture port 18. The septum 15 may be comprised of a polymer material such as a room-temperature vulcanizing (RTV) silicone. In use a syringe needle (not shown) is inserted through the septum puncture port 18 and punctures the septum 15 to fill the distal sheath lumen 4 with an ultrasonically transparent fluid such as a sterile saline solution. Upon withdrawal of the syringe needle the septum 15 seals itself. The use of a self-sealing septum prevents the pulling of fluids such as air into the distal sheath as the imaging core 10 translates towards the proximal end.

The balloon catheter is sufficiently small, generally 15 Fr or smaller, such that the esophagus is accessed by a nasal route. The balloon envelope 70 may be formed of a compliant polymer blend such as polyethylene/EVA and is attached, generally by bonding or fusing, to the distal catheter sheath section proximal and distal to the inflation port. The balloon assembly may be 2 cm to 10 cm in length, generally 6 cm. The balloon envelope 70 may be inflated using an ultrasonically transparent fluid, such as a sterile saline solution. The balloon can be inflated up to 4 cm in diameter, generally between 2 cm and 3 cm. The inflated balloon facilitates imaging of the esophageal wall and cardiac structures.

Figure 4:
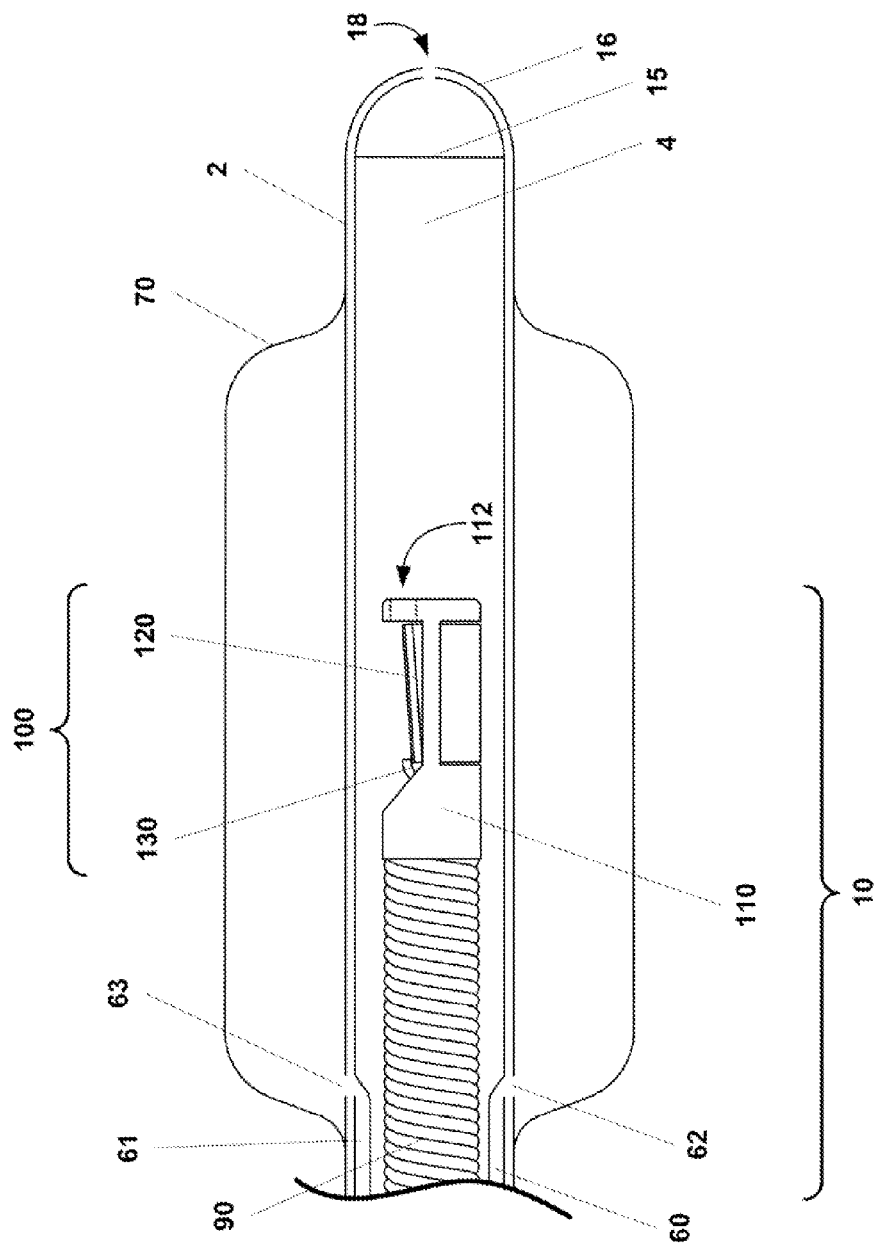
FIG. 4 is a side view in partial cross section of the distal section of another transesophageal echocardiography balloon catheter embodying the present invention.

Referring now to FIG. 4, a side view of an alternative embodiment of a distal section of a transesophageal echocardiography catheter is shown. The distal section comprises a balloon envelope 70, an inflation lumen 60, an inflation port 62, a deflation lumen 61, a deflation port 63, and an ultrasonic imaging core 10. The ultrasonic imaging core 10 comprises a drive cable 90 and a distal housing assembly 100 further comprising a distal housing 110, a transducer stack 120, and a transmission line 130. The distal housing 110 further comprises a distal opening 112 that facilitates fluid flow across the face of the transducer stack. The transducer stack 120 can be focused or unfocused. An exemplary transducer for a 15 Fr sized catheter has a circular aperture of up to approximately 4.2 mm and has a focal length between 1 cm and 4 cm, generally between 2 cm and 3 cm. Methods to focus transducers are known to those skilled in the art of transducer fabrication.

The distal section of the balloon imaging catheter further comprises a sheath 2, a distal sheath lumen 4, a septum 15, an atraumatic distal tip 16, and a septum puncture port 18. The septum 15 may be comprised of a polymer material such as a room-temperature vulcanizing (RTV) silicone. A syringe needle (not shown) is inserted through the septum puncture port 18 and punctures the septum 15 to fill the distal sheath lumen 4 with an ultrasonically transparent fluid such as a sterile saline solution. Upon withdrawal of the syringe needle the septum 15 seals itself. The use of a self-healing septum prevents pulling fluids such as air into the distal sheath as the imaging core 10 translates towards the proximal end.

The balloon catheter is sufficiently small, generally 15 Fr or smaller, such that the esophagus is accessed by a nasal route. The balloon envelope 70 is formed of a compliant polymer blend such as polyethylene/EVA and is attached, generally by bonding or fusing, to the distal catheter sheath section proximal and distal to the inflation port 62. The balloon assembly may be 2 cm to 10 cm in length, generally 6 cm. The balloon envelope 70 may be inflated using an ultrasonically transparent fluid, such as a sterile saline solution. The balloon can be inflated up to 4 cm in diameter, generally between 2 cm and 3 cm. The inflated balloon facilitates imaging of the esophageal wall and cardiac structures. An active inflation/deflation loop enables circulation of a sterile saline solution. The circulating saline can potentially be used to remove heat at the esophageal wall and prevent the formation of an atrio-esophageal fistula.

Figure 5:
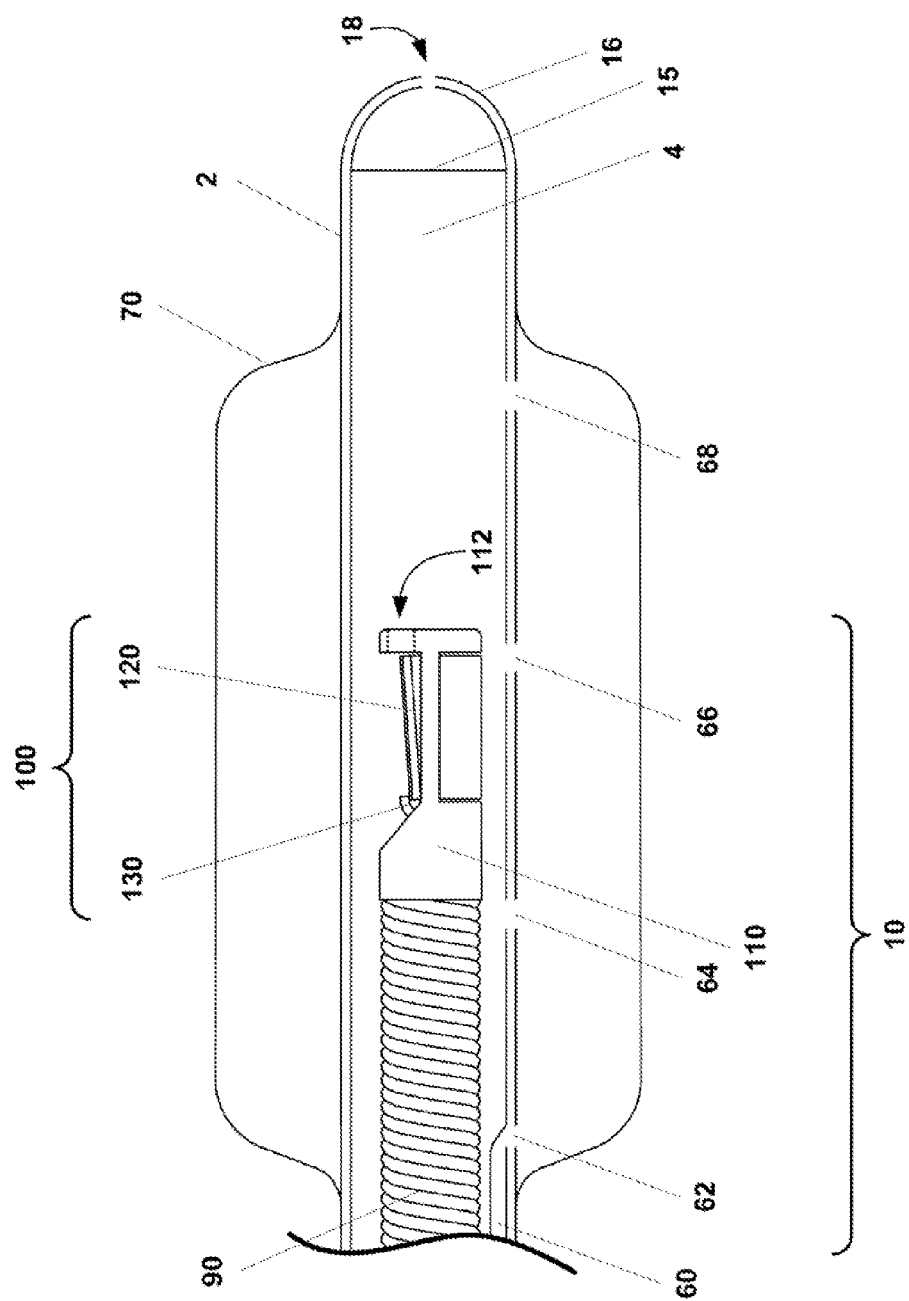
FIG. 5 is a side view of the distal section of a transesophageal echocardiography balloon catheter according to a further embodiment of the present invention.

Referring now to FIG. 5, a side view of another embodiment of the distal section of a transesophageal echocardiography catheter is shown. The distal section comprises a balloon envelope 70, an inflation lumen 60, an inflation port 62, and an ultrasonic imaging core 10. The ultrasonic imaging core 10 comprises a drive cable 90 and a distal housing assembly 100 further comprising a distal housing 110, a transducer stack 120, and a transmission line 130. The distal housing 110 further comprises a distal opening 112 that facilitates fluid flow across the face of the transducer stack. The transducer stack 120 can be focused or unfocused. An exemplary transducer for a 15 Fr sized catheter has a circular aperture of up to approximately 4.2 mm and has a focal length between 1 cm and 4 cm, generally between 2 cm and 3 cm. Methods to focus transducers are known to those skilled in the art of transducer fabrication.

The distal section of the balloon imaging catheter further comprises a sheath 2, a distal sheath lumen 4, a septum 15, an atraumatic distal tip 16, and a septum puncture port 18. The septum 15 may be comprised of a polymer material such as a room-temperature vulcanizing (RTV) silicone. A syringe needle (not shown) is inserted through the septum puncture port 18 and punctures the septum 15 to fill the distal sheath lumen 4 with an ultrasonically transparent fluid such as a sterile saline solution. Upon withdrawal of the syringe needle the septum 15 seals itself. The use of a self-sealing septum prevents pulling fluids such as air into the distal sheath as the imaging core 10 translates towards the proximal end.

The balloon catheter is sufficiently small, generally 15 Fr or smaller, such that the esophagus is accessed by a nasal route. The balloon envelope 70 may be formed of a compliant polymer blend such as polyethylene/EVA and is attached, generally by bonding or fusing, to the distal catheter sheath section proximal and distal to the inflation port 62. The balloon assembly may be 2 cm to 10 cm in length, generally 6 cm. The balloon envelope 70 may be inflated using an ultrasonically transparent fluid, such as a sterile saline solution. The balloon can be inflated up to 4 cm in diameter, generally between 2 cm and 3 cm. The inflated balloon facilitates imaging of the esophageal wall and cardiac structures. Fluid exchange ports 64, 66, 68 between the distal shaft lumen 4 and interior of the balloon envelope enable exchange of the ultrasonically transparent fluid as the imaging core 10 is advanced and retracted. The fluid exchange ports effectively provide a fluid reservoir that prevents the potential generation of negative pressures as the imaging core 10 is retracted within the distal section sheath 2.

Figure 6:
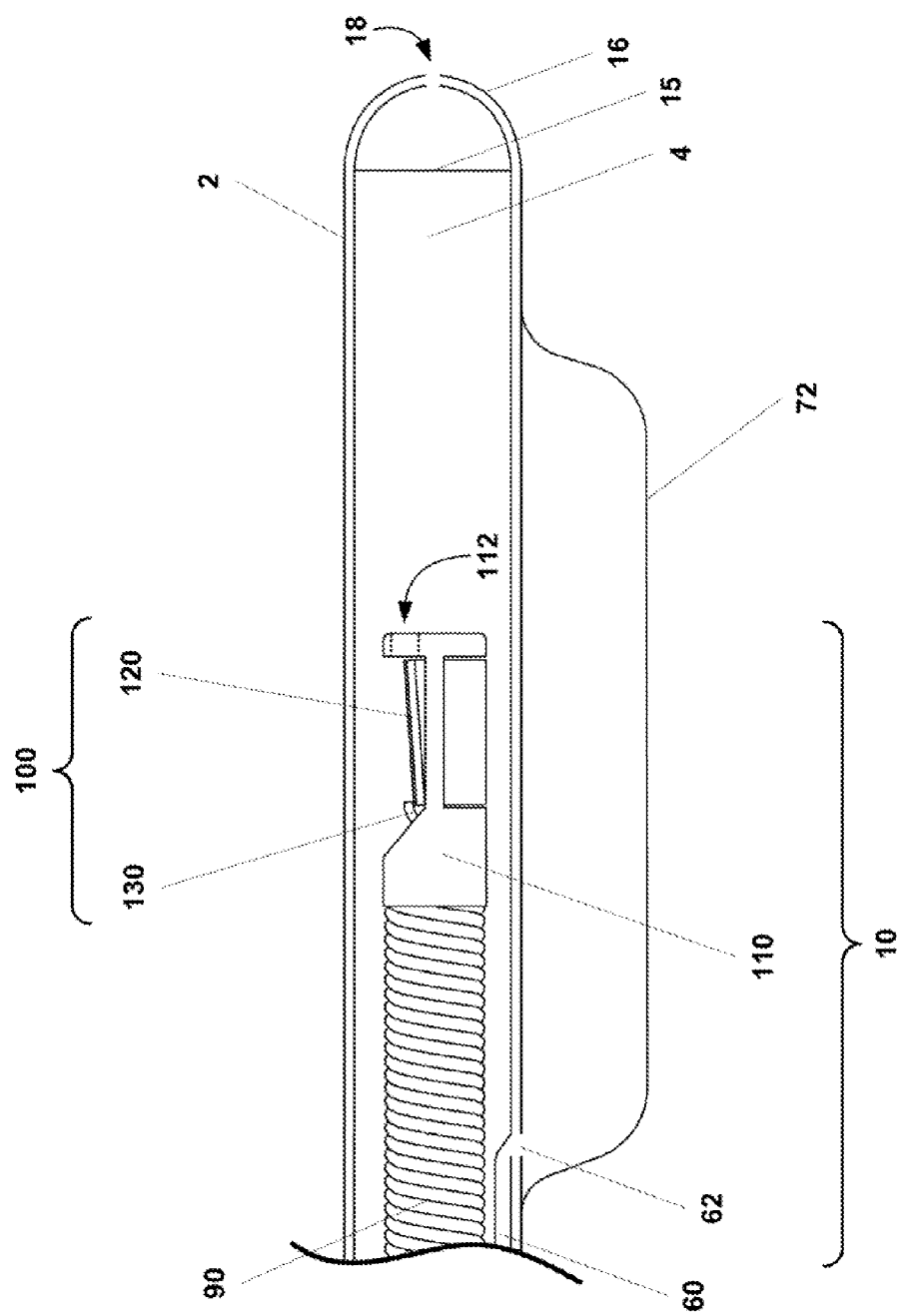
FIG. 6 is a side view of the distal section of a transesophageal echocardiography balloon catheter according to a still further embodiment of the present invention.

Referring now to FIG. 6, a side view of still another embodiment of the distal section of a transesophageal echocardiography catheter is shown. The distal section of the catheter comprises a balloon envelope 72, an inflation lumen 60, an inflation port 62, and an ultrasonic imaging core 10. The ultrasonic imaging core 10 comprises a drive cable 90 and a distal housing assembly 100 further comprising a distal housing 110, a transducer stack 120, and a transmission line 130. The distal housing 110 further comprises a distal opening 112 that facilitates fluid flow across the face of the transducer stack. The transducer stack 120 can be focused or unfocused. An exemplary transducer for a 15 Fr sized catheter has a circular aperture of up to approximately 4.2 mm and has a focal length between 1 cm and 4 cm, generally between 2 cm and 3 cm. Methods to focus transducers are known to those skilled in the art of transducer fabrication.

The distal section of the balloon imaging catheter further comprises a sheath 2, a distal sheath lumen 4, a septum 15, an atraumatic distal tip 16, and a septum puncture port 18. The septum 15 may be comprised of a polymer material such as a room-temperature vulcanizing (RTV) silicone. A syringe needle (not shown) is inserted through the septum puncture port 18 and punctures the septum 15 to fill the distal sheath lumen 4 with an ultrasonically transparent fluid such as a sterile saline solution. Upon withdrawal of the syringe needle the septum 15 seals itself. The use of a self-sealing septum prevents pulling fluids such as air into the distal sheath as the imaging core 10 translates towards the proximal end.

The distal sheath 2 is coupled to the esophageal wall by use of an ultrasonic couplant such as an ultrasonic gel couplant. The catheter is held in position relative to the esophageal wall by inflation of the balloon. The balloon expands typically to the side of the catheter distal from the heart. The balloon catheter is sufficiently small, generally 15 Fr or smaller, such that the esophagus is accessed by a nasal route. The balloon envelope 72 may be formed of a compliant polymer blend such as polyethylene/EVA and is attached, generally by bonding or fusing, to the distal catheter sheath section proximal and distal to the inflation port 62. The balloon assembly may be 2 cm to 10 cm in length, generally 6 cm. The balloon envelope 72 may be inflated using a fluid, such as a radio-opaque contrast medium, sterile saline solution, or mixture thereof. The fluid is not required to be ultrasonically transparent, because the inflation balloon is posterior to the imaging core and esophageal wall. The inflated balloon facilitates imaging of the esophageal wall and cardiac structures.

Figure 7:
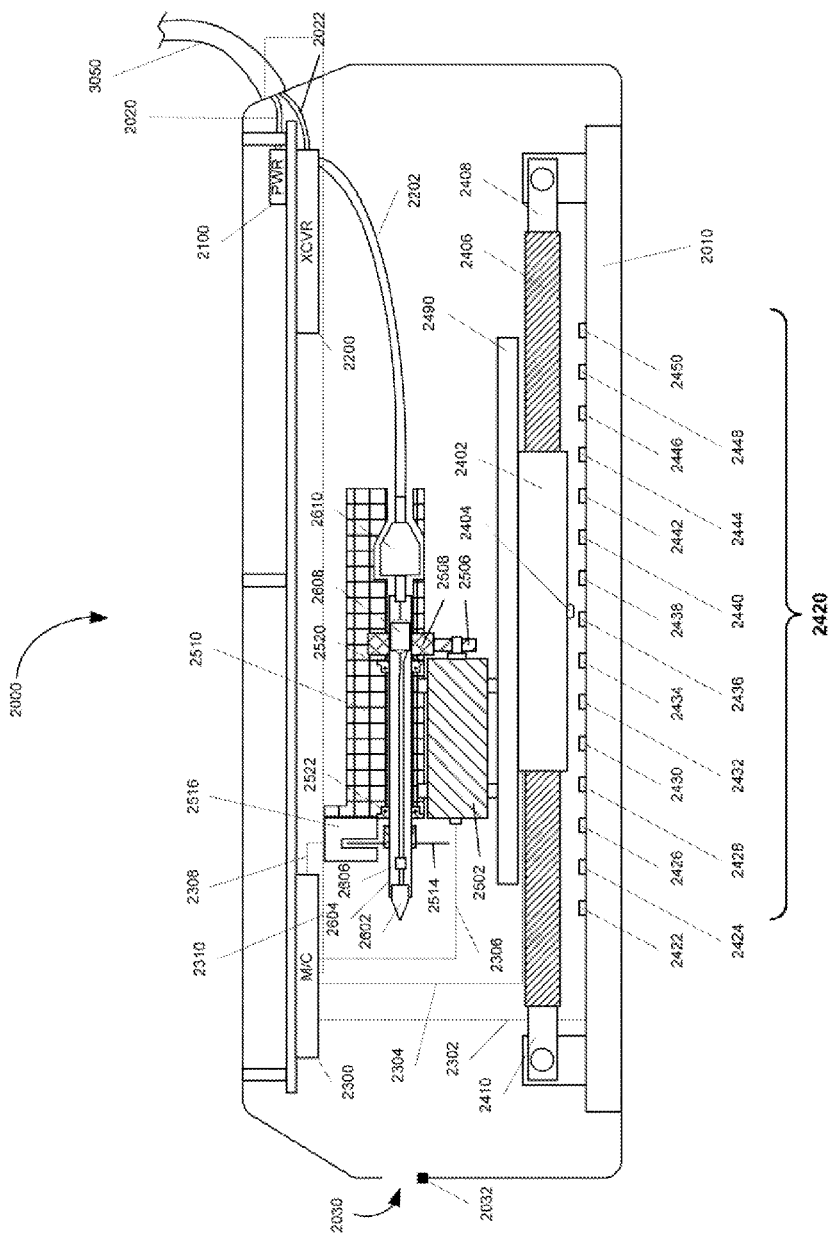
FIG. 7 is a side view of a patient interface module embodying aspects of the present invention.
Figure 8:
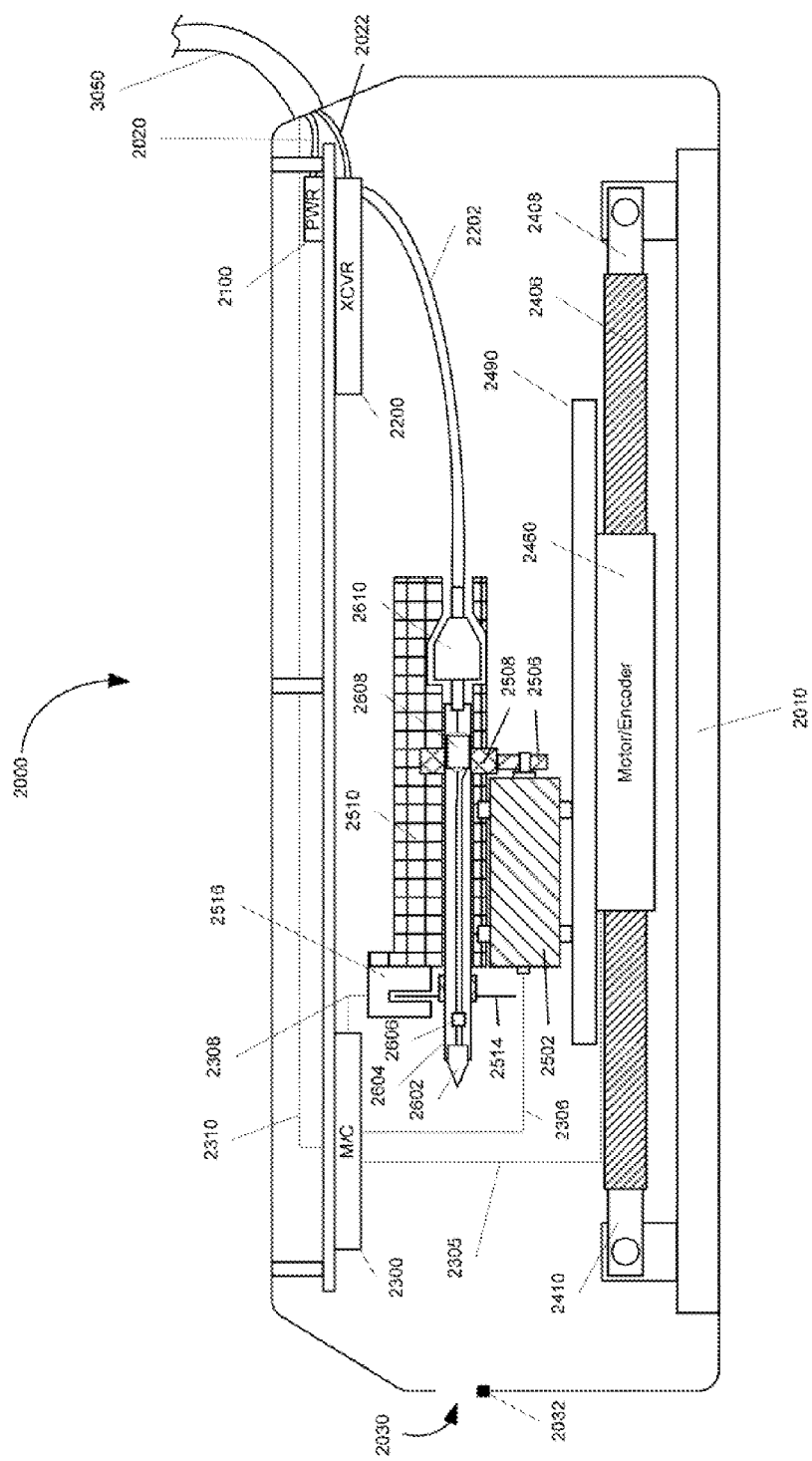
FIG. 8 is a side view of another patient interface module embodying aspects of the present invention.
Figure 9:
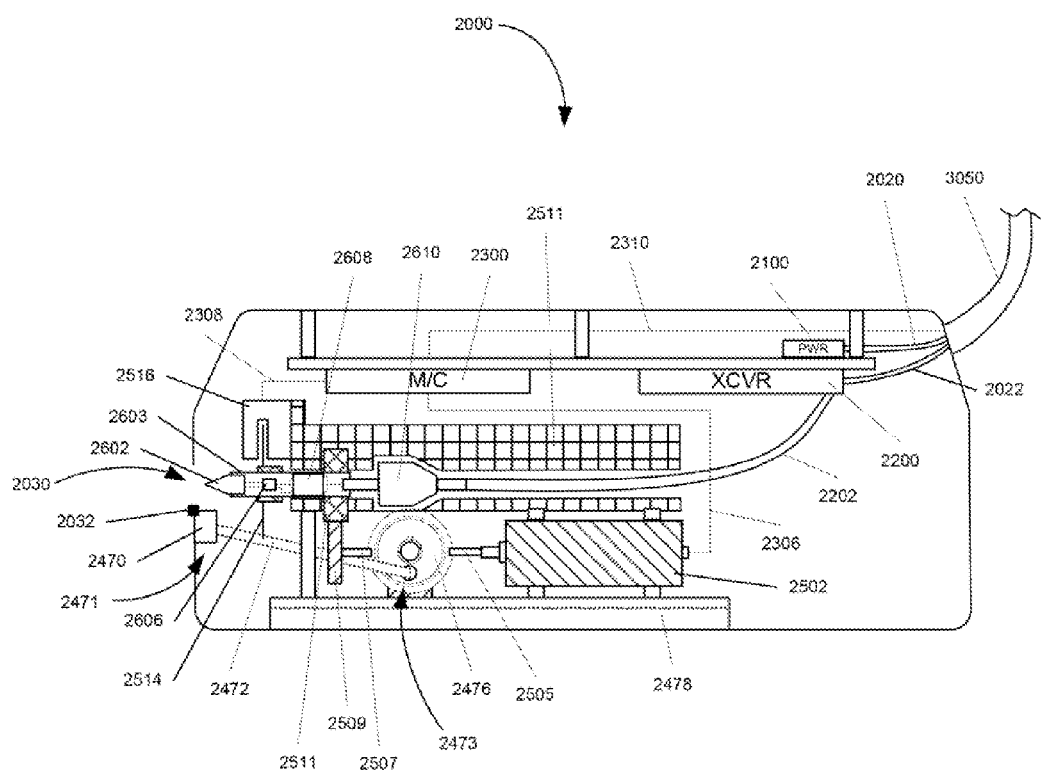
FIG. 9 is a side view of a further patient interface module embodying aspects of the present invention.

Referring now to FIGS. 7-9, several embodiments of the patient interface module are illustrated. The patient interface module is the electro-mechanical interface between the catheter and the imaging engine. The patient interface module contains the ultrasound generator, receiver, and scanning mechanism. FIG. 7 shows a side view of one embodiment of the patient interface module 2000. The patient interface module 2000 is in mechanical and electrical communication with the ultrasound imaging core (not shown) of the imaging catheter. The patient interface module 2000 comprises means for linear translation and rotation of the ultrasound imaging core. The proximal end of the telescoping section of the catheter is attached to an anchor mount 2032. A rotator 2602 mechanically and electrically couples to the proximal end of the catheter imaging core and enables both rotation and linear translation of the catheter imaging core.

The patient interface module 2000 further comprises a power board 2100, a transceiver (XCVR) board 2200, a motion control (M/C) module 2300, and a linear position sensing array 2420. The power board 2100 is in electrical communication (not shown) with the transceiver board 2200, the motion control module 2300, and a linear position sensing array 2420.

The motion control module 2300 comprises electronics that are in electrical communication 2302, 2304, 2306, 2308 with a linear piezomotor 2402, the linear position sensing array 2420, a rotational motor 2502, and a rotational encoder reader 2516. The motion control module 2300 is additionally in electrical communication 2310, 3050 with the imaging engine (not shown) and provides position information. The motion control module 2300 may still additionally be in electrical communication with a set of patient interface module operation control buttons (not shown) which are located on an external surface of the patient interface module.

The linear piezomotor comprises a motor housing 2402, a rod 2406, and flat springs 2408, 2410. Advantages of piezomotors comprise low mass, rapid acceleration and deceleration, bidirectional translation (or cycling), and high velocities (up to 450 mm/s). The piezomotor housing 2402, a translation stage 2490, a rotational motor 2502, and a mounting block 2510 are rigidly fixed. The piezomotor housing 2402 and fixedly attached components such as the translation stage 2490 move along the rod 2406.

The rotational motor 2502 is mechanically coupled to first and second gears 2506, 2508. Alternatively, the rotational motor 2502 may be mechanically coupled to first and second pulleys. The rotational motor 2502 enables continuous rotation of the ultrasound imaging core. Rotational motors operate at up to at least 8000 revolutions per minute (RPM). The second gear 2508 is fixedly attached to a drive shaft 2604. The drive shaft further comprises the rotator 2602.

The drive shaft 2604 is housed within the mounting block 2510. The mounting block may be machined or cast from a light-weight material, such as aluminum or titanium, and may additionally provide electrical shielding. An encoder wheel 2514 is also fixedly attached to the drive shaft 2604 whereupon an encoder reader 2516 can read the position of the encoder wheel 2514. The encoder wheel 2514 and encoder reader 2516 enable tracking of the rotational position of the drive shaft 2604.

The linear position sensing system comprises an array 2420 of anisotropic magneto-resistive (AMR) sensors 2422-2450 and a permanent magnet 2404. The permanent magnet 2404 is fixedly attached to the piezomotor housing 2402. The array 2420 enables accurate and precise position sensing of the permanent magnet 2404. The relative axial position of distal housing and transducer stack of the catheter imaging core can be determined, because the catheter imaging core is mechanically coupled to the piezomotor housing 2402 and permanent magnet 2404. The AMR sensors are positioned periodically along the travel range and offset from the magnet. The spacing between the AMR sensors can be up to 8 mm. AMR sensors can be added to extend the travel range of position sensing. The offset distance of the sensors to the permanent magnet depends on the field strength at the pole face of the magnet. The offset distance can be up to 0.25" for ceramic and AlNiCo magnets and up to 0.5" for rare earth magnets, such as neodymium types. Resolution of position is approximately 0.002" (50 μm) with accuracy better than 1% with an AMR sensor spacing of 8 mm. Resolution and accuracy can be improved by reducing sensor spacing.

The transceiver board 2200 comprises analog electronics for transmission and reception of the ultrasound signals. The transceiver board 2200 is in electrical communication 2022, 3050 with the imaging engine (not shown). The transceiver board 2200 is additionally in electrical communication 2202 with a liquid metal rotary coupler 2610 and the drive shaft 2604. The electrical components of the drive shaft 2604 comprise an electrical jack 2608, a transformer 2606, and an electrical contact assembly (not shown) within the rotator 2602. The electrical contact assembly is in electrical communication with the transmission line of the catheter imaging core.

Referring now to FIG. 8, a side view of another embodiment of the patient interface module 2000 is shown. The patient interface module 2000 is in mechanical and electrical communication with the ultrasound imaging core (not shown) of the imaging catheter. The patient interface module 2000 comprises means for linear translation and rotation of the ultrasound imaging core. The proximal end of the telescoping section of the catheter is attached to an anchor mount 2032. A rotator 2602 mechanically couples to the proximal end of the catheter imaging core and enables both rotation and linear translation of the catheter imaging core.

The patient interface module 2000 further comprises a power board 2100, a transceiver (XCVR) board 2200, and a motion control (M/C) module 2300. The power board 2100 is in electrical communication (not shown) with the transceiver board 2200 and the motion control module 2300.

The motion control module 2300 comprises electronics that are in electrical communication 2305, 2306, 2308 with a linear piezomotor and encoder system 2460, a rotational motor 2502, and a rotational encoder reader 2516. The motion control module 2300 is additionally in electrical communication 2310, 3050 with the imaging engine (not shown) and provides position information. The motion control module 2300 may still additionally be in electrical communication with a set of patient interface module operation control buttons (not shown) which are located on an external surface of the patient interface module.

The linear piezomotor comprises a motor housing 2460, a rod 2406, and flat springs 2408, 2410. Advantages of piezomotors comprise low mass, rapid acceleration and deceleration, bidirectional translation (or cycling), and high velocities (up to 450 mm/s). The linear piezomotor and encoder system housing 2460, a translation stage 2490, a rotational motor 2502, and a mounting block 2510 are rigidly fixed. The linear piezomotor and encoder system housing 2460 and fixedly attached components such as the translation stage 2490 move along the rod 2406. The rotational motor 2502 is mechanically coupled to first and second gears 2506, 2508. Alternatively, the rotational motor 2502 may be mechanically coupled to first and second pulleys.

The rotational motor 2502 enables continuous rotation of the ultrasound imaging core. Rotational motors operate at up to at least 8000 revolutions per minute (RPM). The second gear 2508 is fixedly attached to a drive shaft 2604. The drive shaft further comprises the rotator 2602. The linear encoder system enables tracking of the axial position of the drive shaft 2604.

The drive shaft 2604 is housed within the mounting block 2510. The mounting block may be machined or cast from a light-weight material, such as aluminum or titanium, and may additionally provide electrical shielding. An encoder wheel 2514 is also fixedly attached to the drive shaft 2604 whereupon an encoder reader 2516 can read the position of the encoder wheel 2514. The encoder wheel 2514 and encoder reader 2516 enable tracking of the rotational position of the drive shaft 2604.

The transceiver board 2200 comprises analog electronics for transmission and reception of the ultrasound signals. The transceiver board 2200 is in electrical communication 2022, 3050 with the imaging engine (not shown). The transceiver board 2200 is additionally in electrical communication 2202 with a liquid metal rotary coupler 2610 and the drive shaft 2604. The electrical components of the drive shaft 2604 comprise an electrical jack 2608, a transformer 2606, and an electrical contact assembly (not shown) within the rotator 2602. The electrical contact assembly is in electrical communication with the transmission line of the catheter imaging core.

Referring now to FIG. 9, a side view of still another embodiment of the patient interface module 2000 is shown. The patient interface module 2000 is in mechanical and electrical communication with the ultrasound imaging core (not shown) of the imaging catheter. The patient interface module 2000 comprises means for linear translation and rotation of the ultrasound imaging core. The proximal end of the telescoping section of the catheter is attached to an anchor mount 2032. A drive shaft 2603 rotator 2602 mechanically and electrically couples to the proximal end of the catheter imaging core and enables both rotation and linear translation of the catheter imaging core.

The patient interface module 2000 further comprises a power board 2100, a transceiver (XCVR) board 2200, and a motion control (M/C) module 2300. The power board 2100 is in electrical communication (not shown) with the transceiver board 2200 and the motion control module 2300.

The motion control module 2300 comprises electronics that are in electrical communication 2306, 2308 with a rotational motor 2502 and a rotational encoder reader 2516. The motion control module 2300 is additionally in electrical communication 2310, 3050 with the imaging engine (not shown) and provides position information. The motion control module 2300 may further be in electrical communication with a set of patient interface module operation control buttons (not shown) which are located on an external surface of the patient interface module. The relative linear position of a low-friction translation stage 2478 and catheter imaging core is determined from the rotational position. Alternatively, a linear position sensor, such as the linear position sensing system as illustrated in FIG. 3, can be included to reduce ambiguity of longitudinal position of the catheter imaging core.

The rotational motor 2502 is mechanically coupled to a first pinion gear 2505. The first pinion gear engages a first gear 2476. The first gear 2476 engages a second pinion gear 2507. The first gear 2476 is also fixedly attached to a first end 2473 of a linkage arm 2472. A second end 2471 of the linkage arm 2472 is fixedly attached to a linkage arm mount 2470. The first gear 2476 and rotational motor 2502 are fixedly attached to a low-friction translation stage 2478. The second pinion gear 2507 is fixedly attached to a second gear 2509. The second gear 2509 engages a third gear 2511 that is fixedly attached to the drive shaft 2603. Alternatively, first and second pulleys can be used in place of the second and third gears 2507, 2509.

The rotational motor 2502 enables continuous rotation and translation of the ultrasound imaging core. As the first pinion gear 2505 rotates, the first gear 2476 and first end 2473 of the linkage arm 2472 rotate about the axis of rotation of the first gear 2476. The cyclical motion of the linkage arm 2472 causes the low-friction translation stage 2478 to slide back and forth. The back-and-forth motion of the low-friction translation stage 2478 causes the imaging core to correspondingly translate back and forth, or cycle in a longitudinal direction. The range of linear translation will be determined by the distance of the first end 2473 of the linkage arm 2472 to the axis of rotation of the first gear 2476. Advantages of a gear and linkage arm system compared to embodiments comprising a linear translation motor include in part a simpler design, lower weight, and lower cost.

The drive shaft 2603 is housed within the mounting block 2511. The mounting block may be machined or cast from a light-weight material, such as aluminum or titanium, and may additionally provide electrical shielding. An encoder wheel 2514 is also fixedly attached to the drive shaft 2603 whereupon an encoder reader 2516 can read the position of the encoder wheel 2514. The encoder wheel 2514 and encoder reader 2516 enable tracking of the rotational position of the drive shaft 2604.

The transceiver board 2200 comprises analog electronics for transmission and reception of the ultrasound signals. The transceiver board 2200 is in electrical communication 2022, 3050 with the imaging engine (not shown). The transceiver board 2200 is additionally in electrical communication 2202 with a liquid metal rotary coupler 2610 and the drive shaft 2603. The electrical components of the drive shaft 2604 comprise an electrical jack 2608, a transformer 2606, and an electrical contact assembly (not shown) within the rotator 2602. The electrical contact assembly is in electrical communication with the transmission line of the catheter imaging core.

A rapid linear translation and rotation of the ultrasound imaging core combined with the accurate position sensing enables volumetric scanning of moving structures such as cardiac structures. Cyclical linear translation enables continuous real-time imaging of a volume of interest. Alternative transducer configurations can provide additional benefits for image guidance of cardiac ablation procedures.

Figure 10:
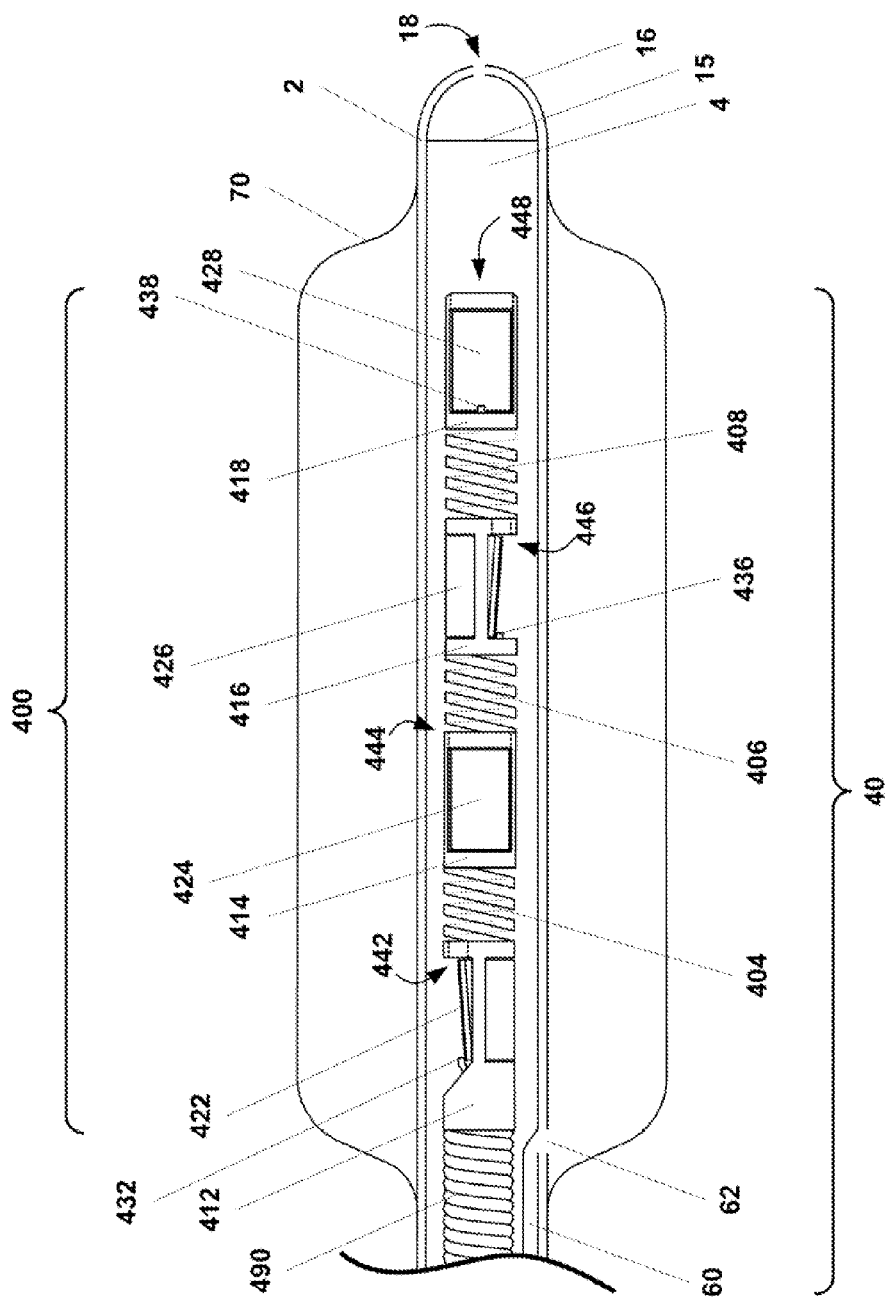
FIG. 10 is a side view in partial cross section of the distal section of a transesophageal echocardiography balloon catheter embodying the present invention.

Referring now to FIG. 10, an embodiment of the distal section of a transesophageal echocardiography catheter comprising a multiple transducer assembly is shown in partial cross section. The distal section of the catheter comprises a balloon envelope 70, an inflation lumen 60, an inflation port 62, and an ultrasonic imaging core 40. The ultrasonic imaging core 40 comprises a drive cable 490 and a distal housing assembly 400. The distal housing assembly 400 comprises four transducer housings 412, 414, 416, 418, four transducer stacks 422, 424, 426, 428, and three flexible housing couplings 404, 406, 408. The four transducer housings further comprise distal openings 442, 444, 446, 448 that facilitate fluid flow across the faces of the transducer stacks. The individual transducers and housings are substantially similar in configuration to that shown in FIG. 2.

The multiple transducer assembly can be fabricated according to several techniques. In an exemplary design, the multiple transducer housings and couplings can be fabricated from a single stainless steel hypotube. The transducer housings provide rigid support to the individual transducer assemblies by means of a fitted slot. The couplings are spiral-cut sections of the hypotube and balance axial rigidity and bending flexibility for the multiple transducer assembly. The pitch of the spiral cut can be constant or can be varied depending upon the target stiffness characteristics. The pitch may be increased for less flexibility or decreased for more flexibility. Some flexibility facilitates transnasal positioning of the catheter. In an exemplary design, the transducer housings are approximately 4 mm in length, the transducer couplings are approximately 6 mm in length, and the transducer diameters are 2.5 mm. The pitch of spiral-cut coupling is typically 1 mm having 100 micron kerfs. In an alternative embodiment of the multiple transducer assembly, the transducer housing couplings can be separate materials such as stainless steel drive cables that are attached to the transducer housings.

As illustrated in FIG. 10, the directions of nearest-neighbor transducers are offset by 90° relative to each other. The first transducer stack 422 faces the top of the drawing sheet, the second transducer stack 424 faces into the drawing sheet, the third transducer stack 426 faces the bottom of the drawing sheet and the fourth transducer stack 428 faces out of the drawing sheet. The rotational offsets of the multiple transducers minimize potential cross interference of tissue-scattered ultrasonic energy between transducers. Advantages of a multiple transducer assembly comprise increased 3D imaging frame rate. The cyclic linear translation travel range of the transducer assembly can be decreased according to the number of transducers and transducer separation distance. The complete 3D image can be formed from the smaller 3D images from the individual transducers. For the exemplary configuration shown in FIG. 10 and an image volume comprising a 4 cm height, a travel path of approximately 1 cm is required. This leads to an increase in frame rate by a factor of approximately four compared to that of a single element transducer assembly.

The distal section of the balloon imaging catheter further comprises a sheath 2, a distal sheath lumen 4, a septum 15, an atraumatic distal tip 16, and a septum puncture port 18. The septum 15 is comprised of a polymer material such as a room-temperature vulcanizing (RTV) silicone. A syringe needle (not shown) is inserted through the septum puncture port 18 and punctures the septum 15 to fill the distal sheath lumen 4 with an ultrasonically transparent fluid such as a sterile saline solution. Upon withdrawal of the syringe needle the septum 15 seals itself. The use of a self-sealing septum prevents the pulling of fluids such as air into the distal sheath as the imaging core 10 translates towards the proximal end.

The balloon catheter is sufficiently small, generally 15 Fr or smaller, such that the esophagus is accessed by a nasal route. The balloon envelope 70 is formed of a compliant polymer blend such as polyethylene/EVA and is attached, generally by bonding or fusing, to the distal catheter sheath section proximal and distal to the inflation port 62. The balloon assembly is 2 cm to 10 cm in length, generally 6 cm. The balloon envelope 70 is inflated using an ultrasonically transparent fluid, such as a sterile saline solution. The balloon can be inflated up to 4 cm in diameter, generally between 2 cm and 3 cm. The inflated balloon facilitates imaging of the esophageal wall and cardiac structures.

Figure 11:
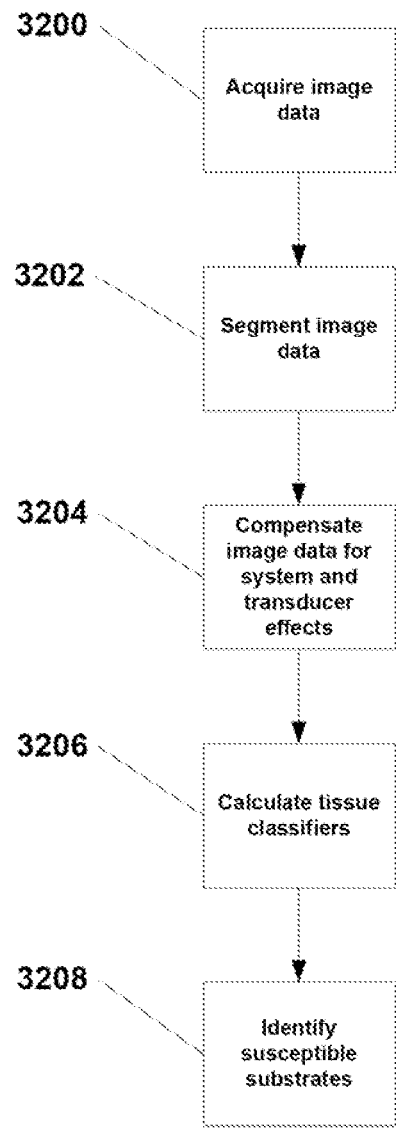
FIG. 11 illustrates a set of processing stages for identifying susceptible substrates according to an embodiment of the present invention.

Referring now to FIG. 11, an exemplary set of processing stages are shown for identifying susceptible substrates in the left atrial wall by means of a transesophageal echocardiography catheter and system as described heretofore. The image data is first acquired in step 3200. The cardiac wall is then segmented in step 3202 from the surrounding tissue and devices, including for example blood in the left atrial chamber, the esophageal wall, the fat pad, and ablation devices. The segmented image data is then, in step 3204, compensated for system and transducer effects comprising range-dependent amplitude and frequency variations. Tissue classifiers are then calculated in step 3206 from segmented image data corresponding to the left atrial wall. Tissue classifiers can be calculated by analysis of the image data and is referred to as time-domain analysis. Tissue classifiers can also be calculated by analysis of the spectral properties of the image data and is referred to as frequency-domain analysis. Exemplary tissue classifiers may comprise integrated backscatter and slope-of-attenuation which are known to those skilled in the art of ultrasonic tissue classification. One approach to tissue classification that is known to those skilled in the art is to select volumetric regions of interest (ROIs) comprised of samples from neighboring image vectors. The number of samples and number of vectors is instrument and application dependent. For example, a ROI from image data that is approximately 1 mm×1 mm×1 mm in volume at a range of 2 cm from a multiple transducer assembly as illustrated in FIG. 10 requires 5 vectors×129 samples×1 slice assuming 0.7° in-plane vector spacing, $100 \times 10^6$ samples/s sampling rate, and a 2 mm slice thickness. Tissue classifiers are then calculated from the compensated image data. Susceptible substrates in the left atrial wall are identified in step 3208 by use of the calculated tissue classifiers. Susceptible substrates are known to be characterized by an increased interstitial fibrotic content. A primary component of the interstitial fibrosis is collagen, and collagen can be identified by its ultrasonic properties. The differentiation of susceptible substrates from normal left atrial wall is determined empirically. Exemplary ultrasound tissue classifiers such as integrated backscatter, slope of attenuation, and speed of sound correlate with collagen content. For patients that are in sinus rhythm, the variation of the tissue classifiers during the heart cycle can also be used to identify susceptible substrates.

Figure 12:
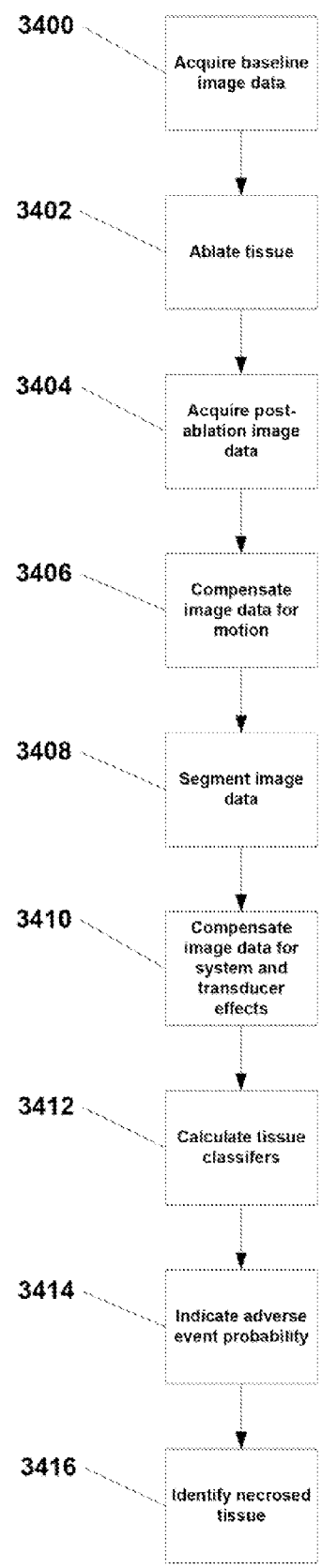
FIG. 12 illustrates a set of processing stages for ablation lesion monitoring and assessment according to an embodiment of the present invention.

FIG. 12 illustrates an exemplary set of processing stages for titrating ablation, indicating potentially adverse events, and identifying necrosed tissue in the left atrial wall that develop as a result of cardiac ablation procedures. Baseline image data of the left atrial wall are acquired in step 3400 prior to ablation in step 3402. Tissue can be ablated by multiple technologies, including RF ablation and cryo-ablation. Post-ablation image data are acquired in step 3404 and evaluated at each ablation site. Pre- and post-ablation image data are co-registered to insure that the same tissue volumes are analyzed. Compensation for motion is provided in step 3406 between image acquisitions as required before co-registration. The left atrial wall is then segmented in step 3408 from the surrounding tissue and devices, including for example blood in the left atrial chamber, the esophageal wall, the fat pad, and ablation devices. The segmented image data is then compensated in step 3410 for system and transducer effects comprising range-dependent amplitude and frequency variations. Tissue classifiers are then calculated in step 3412 from segmented image data corresponding to the left atrial wall. Calculations of integrated backscatter, thermal strain, and slope of attenuation are known to those skilled in the art. Potential adverse events are indicated in step 3414 by means of the calculated tissue classifiers. Adverse event indicators may include microbubble formation, overheating of tissues such as the esophageal wall, and thrombus formation. For example, temperature increases of non-fat tissues correlate with increased echogenicity, larger thermal strains, and decreased slope of attenuation. The ranges of tissue classifiers corresponding to potential adverse events are determined empirically. Necrosed tissues in the left atrial wall are also identified in step 3416 by means of the calculated tissue classifiers. Necrotic tissue is known to be characterized in part by increased echogenicity. For patients that are in sinus rhythm, the variation of the tissue classifiers during the heart cycle can also be used to identify necrosed tissue. The differentiation of necrosed tissue from viable left atrial wall is determined empirically.

The rapid linear translation and rotation of an ultrasound imaging core comprising multiple transducers can increase volumetric imaging rate. Specific imaging algorithms facilitate image guidance for cardiac ablation procedures. Still other configurations of multiple transducers and arrays enable real-time synthetic aperture imaging wherein a synthetic aperture comprises a combination of multiple physical (or real) apertures. Synthetic aperture imaging enables improved image quality. Cyclical linear translation enables continuous real-time 3D synthetic aperture imaging of a volume of interest.

Figure 13:
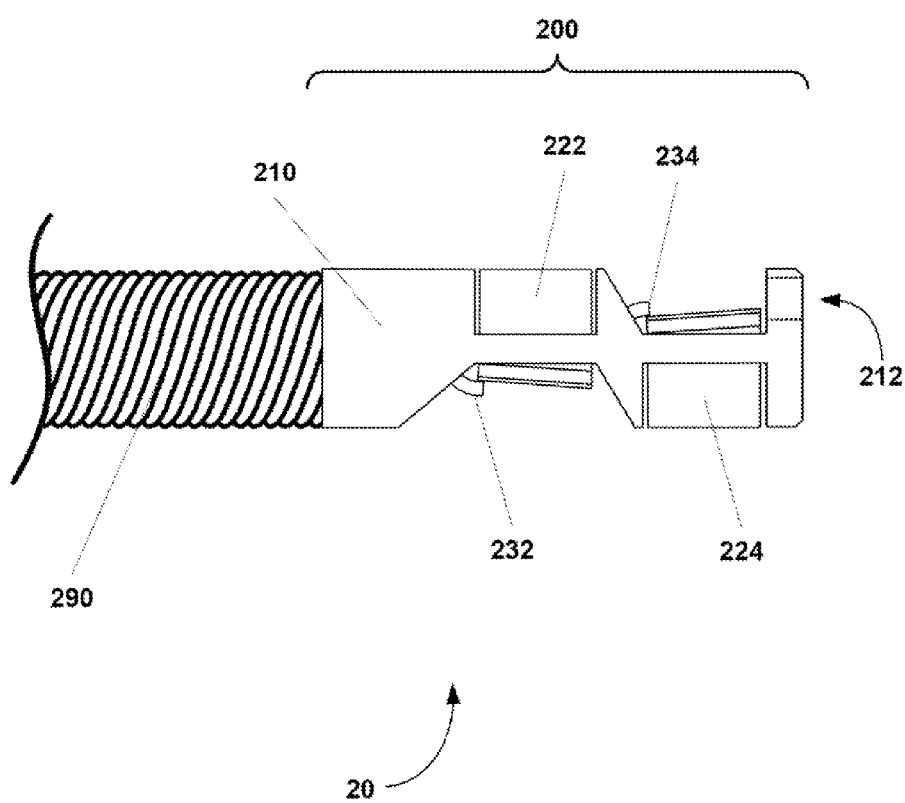
FIG. 13 is a side view of a distal section of an imaging core embodying aspects of the present invention.

Referring now to FIG. 13, a side view of an embodiment of the imaging core 20 of a two transducer assembly is shown. The imaging core 20 comprises a drive cable 290 and a distal housing assembly 200. The distal housing assembly 200 comprises a transducer housing 210, a first transducer stack 222, and a second transducer stack 224. The transducer housing 210 further comprises a distal opening 212 that facilitates fluid flow across the face of the second transducer stack 224. In an exemplary configuration, the transducer housing 210 comprises a laser-cut stainless steel hypotube wherein the first and second transducer stacks 222, 224 are positioned facing in opposing directions. The edge-to-edge inter-element spacing is designed to satisfy synthetic aperture imaging requirements that depend on transducer width, linear translation velocity, rotational velocity, and transmit sequence.

Referring now to FIGS. 14A-14D, one embodiment of a transmit and motion sequence is shown for the two transducer imaging core shown in FIG. 13. The first and second transducer stacks 222, 224 have substantially the same physical properties, including aperture size and imaging frequency. A synthetic aperture 220 is formed as the transmit and motion sequence adds the width of a transducer aperture for each rotation of the imaging core. A full 360° rotation of the imaging core occurs in a time ΔT. The inter-element spacing is half the transducer aperture width. As seen in FIG. 14A, the second transducer stack 224 is fired first (224-1). After the imaging core has rotated 180° (π radians), it has translated distally by half a transducer aperture width as seen in FIG. 14B. The first transducer stack 222 then begins firing (222-1). The imaging core rotates another 180° and translates distally by half a transducer aperture width to the position shown in FIG. 14C. In one full rotation, the imaging core has translated the width of a transducer. The distal transducer then begins its second firing sequence (224-2) as seen in FIG. 14D. Each additional rotation of the imaging core increases the width of the synthetic aperture by a transducer width and enables signal averaging for overlapping subapertures. The effective azimuthal resolution of the synthetic aperture improves as the aperture widens. The transducer widths, inter-element spacing, linear translation velocity, rotational velocity, and transmit sequence can be varied to modify the synthetic aperture size, the number of elements of the synthetic aperture, and the extent of subaperture overlap.

Figure 14:
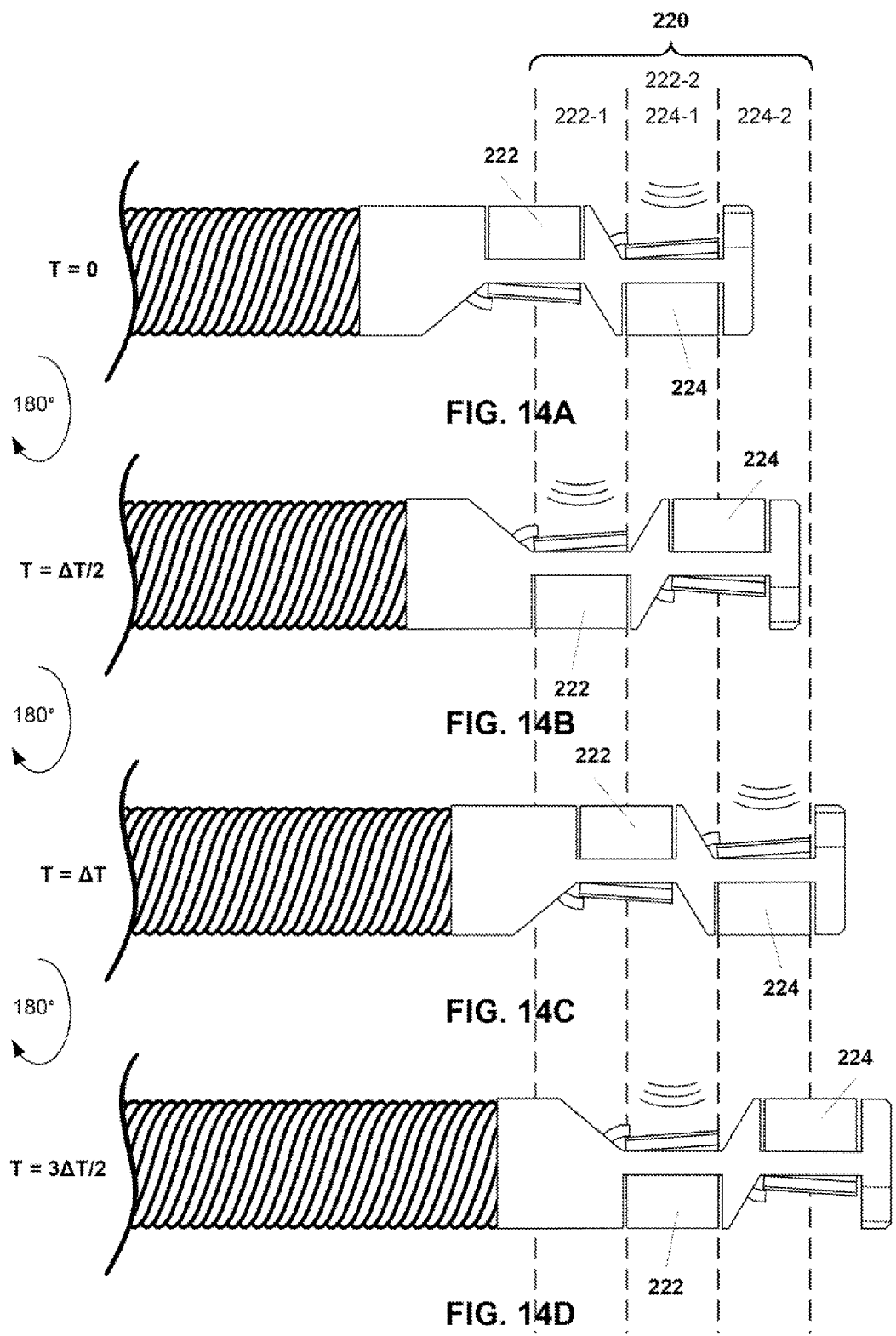
FIGS. 14A-14D illustrate an imaging sequence for synthetic aperture imaging according to an embodiment of the present invention.

For image guidance of AF ablation, a 4 cm field of view may be suitable for intracardiac and transesophageal imaging. The two transducer configuration of the imaging core of FIGS. 13 and 14 are well suited to imaging over a 180° sector rather than a full 360° sector as is done for mechanically rotating imaging catheters used for intravascular ultrasound applications. Each transmit-receive sequence requires approximately 50 μs to acquire. An image frame comprising a 180° sector (angular width) and 256 vectors requires approximately 13 ms to acquire. For a two transducer configuration with 1.6 mm wide transducer and 0.8 mm inter-element spacing, a translation speed of 20 mm/s and rotation speed of 1800 RPM achieves 60 2D frames per second. Each additional rotation acquires two image frames within approximately 25 ms and extends the width of the synthetic aperture by 1.6 mm. For travel distances of 4 cm, the rapid cyclical translation enables continuous 3D image frame rates of approximately two 3D images per second. The 3D image frame rate can be increased by reducing the image range and travel distance.

Figure 15:
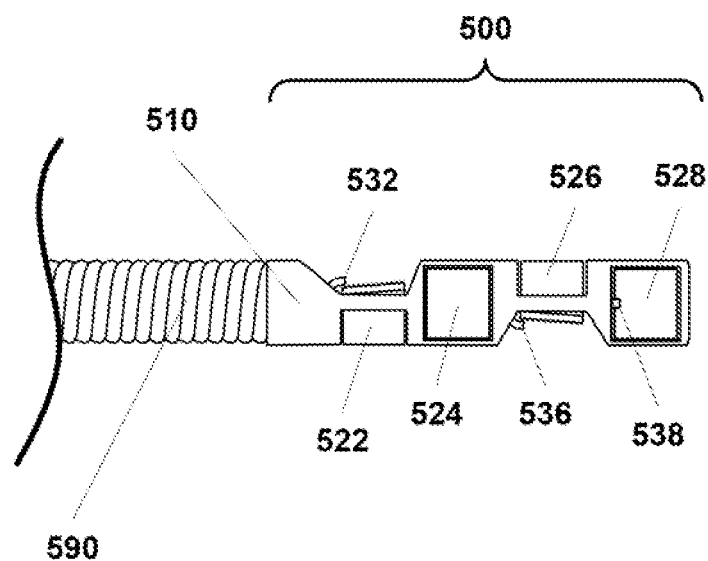
FIG. 15 is a side view of the distal section of an imaging core embodying aspects of the present invention.

Referring now to FIG. 15, a side view of an embodiment of the imaging core 50 comprising a four transducer assembly is shown. The imaging core 50 comprises a drive cable 590 and a distal housing assembly 500. The distal housing assembly comprises a transducer housing 510 and four transducer stacks 522, 524, 526, 528. The four transducer assembly design is well suited for imaging applications that generally display 90° sector frames. The transducer widths, inter-element spacings, linear translation velocity, rotational velocity, and transmit sequence can be varied to modify the synthetic aperture size, the number of elements of the synthetic aperture, and the extent of subaperture overlap. A synthetic aperture with the width of five transducer widths and no subaperture overlap can be achieved when the inter-element spacing is one-half of a transducer width, the imaging core translates the inter-element spacing for each 90° rotation, and the transducers fire in order from the first transducer stack (most distal) 528, the second transducer stack 526, the third transducer stack 524, and then the fourth transducer stack (most proximal) 522.

Figure 16:
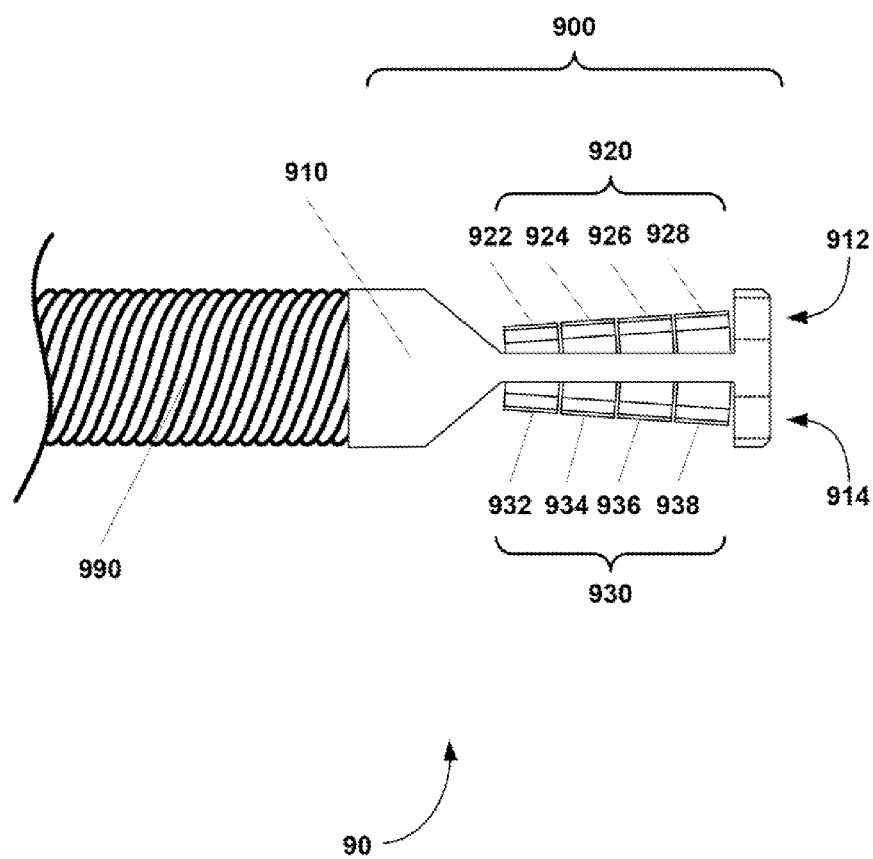
FIG. 16 is a side view of the distal section of a further imaging core embodying aspects of the present invention.

Referring now to FIG. 16, a side view of an embodiment of the imaging core 90 comprising two transducer arrays is shown. The imaging core 90 comprises a drive cable 990 and a distal housing assembly 900. The distal housing assembly 900 comprises a transducer housing 910, a first four element transducer array 920, and a second four element transducer array 930. The first transducer array 920 comprises four independent elements 922, 924, 926, 928 that are substantially mechanically isolated by kerfs. The transducer array 930 comprises four independent elements 932, 934, 936, 938 that are substantially mechanically isolated by kerfs. Each transducer element is attached, generally by soldering or conductive adhesive, to a transmission line (not shown). The transducer elements of each transducer array can be operated independently. The first and second transducer arrays 920, 930 can further be operated independently if there are a sufficient number of signal channels in the imaging engine. The first and second transducer arrays 920, 930 may be multiplexed if signal channels in the imaging engine must be shared.

The transducer arrays are positioned back-to-back. Each transducer can have a separate backing material. Back-to-back transducers can also share a common backing material. The two transducer array assembly 900 can be operated similarly to the two transducer assembly 200 shown in FIG. 13 for continuous, real-time 3D synthetic aperture imaging. Advantages of a transducer array comprise dynamic transmit focusing.

Figures 17A, 17B, 17C:
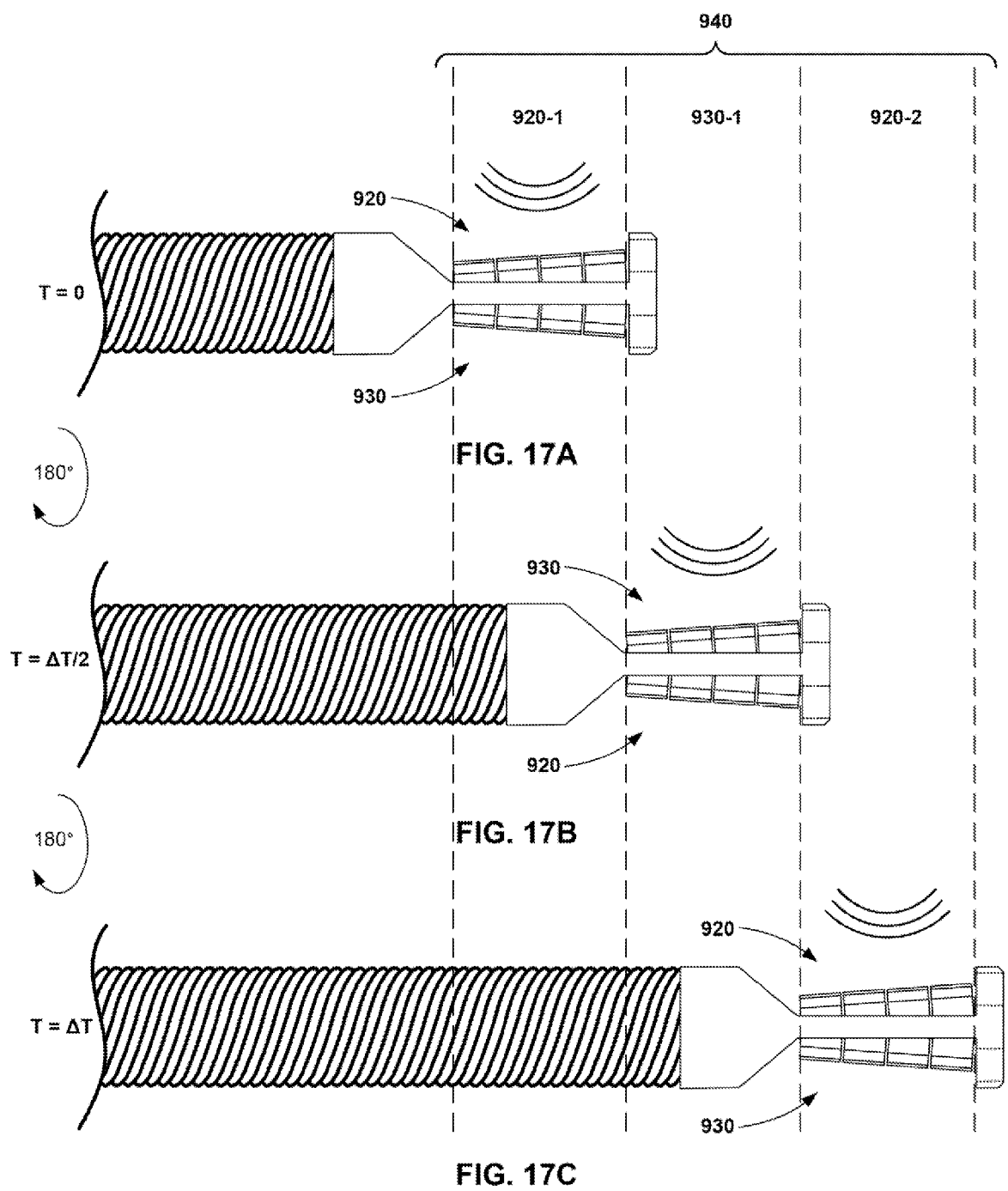
FIGS. 17A-17C illustrate another imaging sequence for synthetic aperture imaging according to aspects of the present invention.

FIGS. 17A-17C illustrate an image sequence for generating a synthetic aperture 940 having a width of three times the transducer array width that is acquired in a single rotation of the imaging core. A full 360° rotation of the imaging core occurs in a time ΔT. The first transducer array 920 is fired first (920-1) over a 180° sector as seen in FIG. 17A. After the imaging core has rotated 180° (π radians), it has translated distally by a transducer array width. The second transducer array 930 then begins firing (930-1) over a 180° sector as seen in FIG. 17B. The imaging core rotates another 180° and translates distally by a transducer array width. In one full rotation, the imaging core has translated the width of two transducer arrays. The distal transducer then begins its second firing sequence (920-2) as seen in FIG. 17C.

In an exemplary intracardiac catheter imaging core, a transducer assembly suitable for continuous, real-time 3D synthetic aperture imaging of cardiac structures comprises a four transducer array with element widths of 0.485 mm and kerf sizes of 20 μm. The transducer array width is 2 mm. A continuous 3D image frame rate of approximately one 3D image per second is achieved with a rotational speed of 1200 RPM and a linear translation velocity of 40 mm/s. A synthetic aperture width of 6 mm comprising 12 elements can be acquired within 50 ms.

In an exemplary transesophageal catheter imaging core, a transducer assembly suitable for continuous, real-time 3D synthetic aperture imaging of cardiac structures comprises a four transducer array with element sizes of approximately 4.2 mm height by 0.5 mm width and kerf sizes of 20 μm. The dimensions of the transducer array are constrained in part by the catheter size. The maximum transducer array height in a 15 Fr catheter is approximately 4.2 mm. The width of the transducer array can vary from 1 mm to 6 mm, generally 2 mm. The kerf width can be as narrow as 5 µm, but is generally 20 µm. For an array with element size of approximately 4.2 mm height by 0.5 mm width and 20 µm kerf widths, the array size is approximately 4.2 mm height by 2 mm width.

Figure 18:
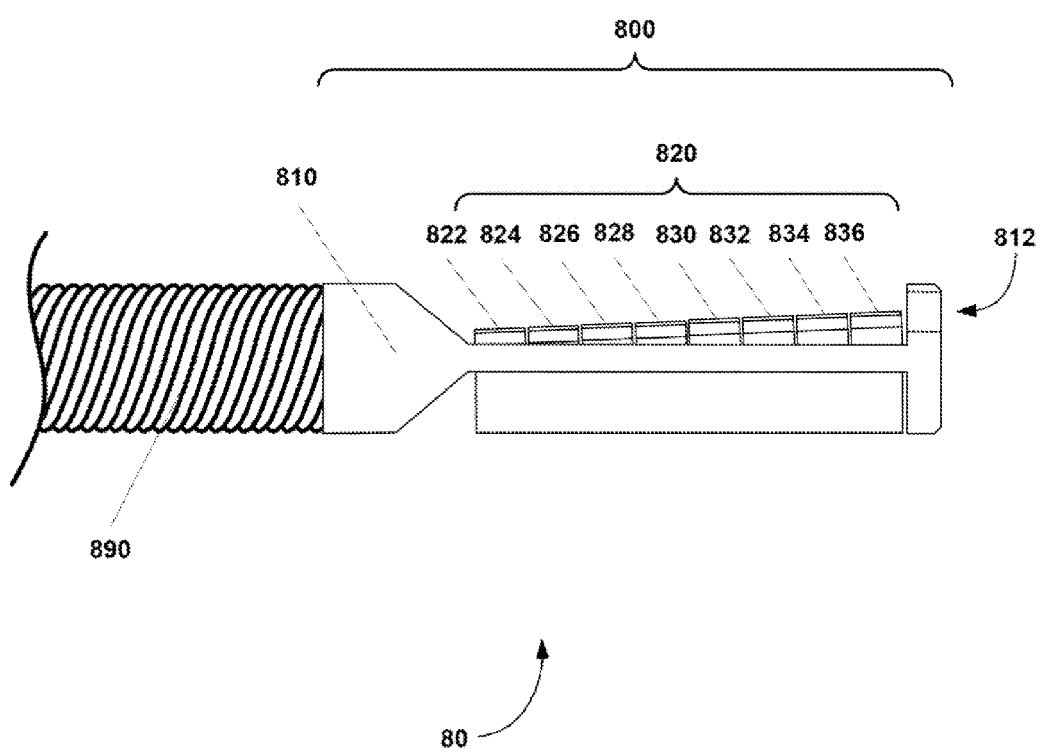
FIG. 18 is a side view of the distal section of another imaging core embodying aspects of the present invention.

Referring now to FIG. 18, a side view of an embodiment of the imaging core 80 of an eight transducer assembly is shown. The imaging core 80 comprises a drive cable 890 and a distal housing assembly 800. The distal housing assembly 800 comprises a distal transducer housing 810 and a transducer array 820. The transducer array 820 comprises eight transducer elements 822, 824, 826, 828, 830, 832, 834, 836 that are substantially mechanically isolated by kerfs. Each transducer element is attached, generally by soldering or conductive adhesive, to a transmission line (not shown). The transducer elements of each transducer array can be operated independently. The eight element transducer array assembly design is well suited for imaging applications that typically display 360° sector frames, similar to a single element transducer shown in FIG. 2. The independent operation of each transducer element enables dynamic transmit focusing that may provide advantages for image quality compared to single element transducer or synthetic aperture imaging.

Figure 19:
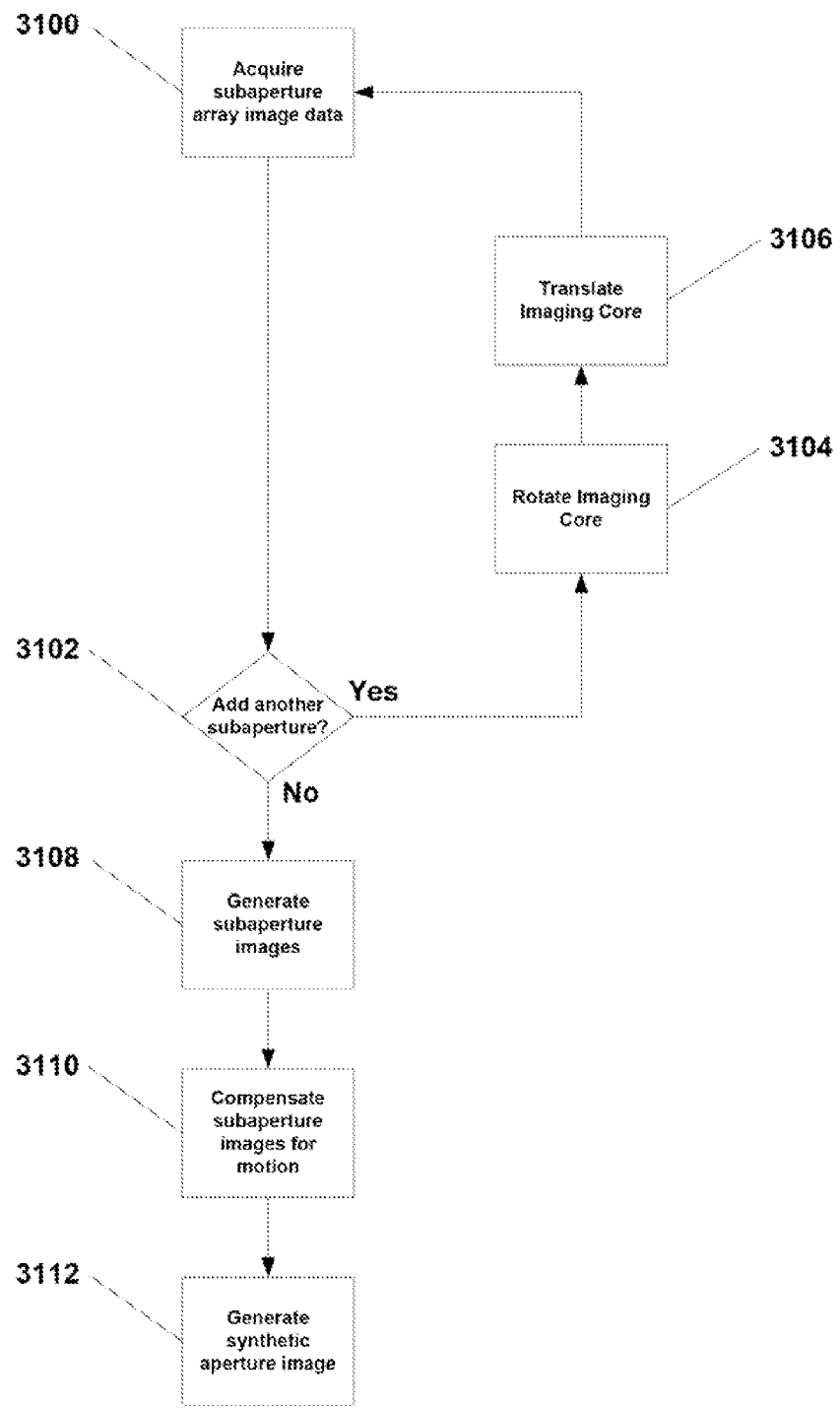
FIG. 19 illustrates a set of processing stages for synthetic aperture imaging according to aspects of the present invention.

FIG. 19 illustrates an exemplary process for generating a synthetic aperture image. The generation and detection of ultrasound energy is known to those skilled in the art. The number of subapertures to be acquired depends in part on the size of the transducer array, the size of the targeted synthetic aperture, and potentially time constraints due to tissue motion. For a transducer array having a 2 mm width and a targeted synthetic aperture width of 4 mm, two subapertures are required. The process of FIG. 19 initiates with step 3100 where subaperture array image data are acquired. If this is the start of the synthetic aperture imaging process and additional subaperture array image data are to be acquired, it is determined in decision block 3102 that another subaperture array image should be added. The imaging core is then rotated in step 3104 and translated in step 3106. The second subaperture is acquired with the repeat of step 3100. The rotation speed and translation speed depends in part on the transducer array configuration, the maximum imaging range, the vector density, and targeted frame rate. The motion speeds further depend on tissue motion. For exemplary case shown in FIG. 14 of the two transducer array assembly 900 having a 2 mm array width, 40 frames per second can be achieved assuming a maximum imaging range of 4 cm, a vector density of 256 scan lines per 180° image sweep, and a rotation speed of 1200 RPM. If no additional subaperture array images need to be acquired, it is determined in decision block 3102 that no additional subaperture array image are to be added to the synthetic aperture. Subaperture images are then generated in step 3108. Tissue motion that occurs between subaperture acquisitions is compensated in step 3110. Motion compensation techniques are known to those skilled in the art and comprise block correlation techniques. A synthetic aperture image is then generated in step 3112 from both subaperture image data sets. Image formation comprises apodization and delay-and-sum beamforming techniques that are known to those skilled in the art.

Figure 20:
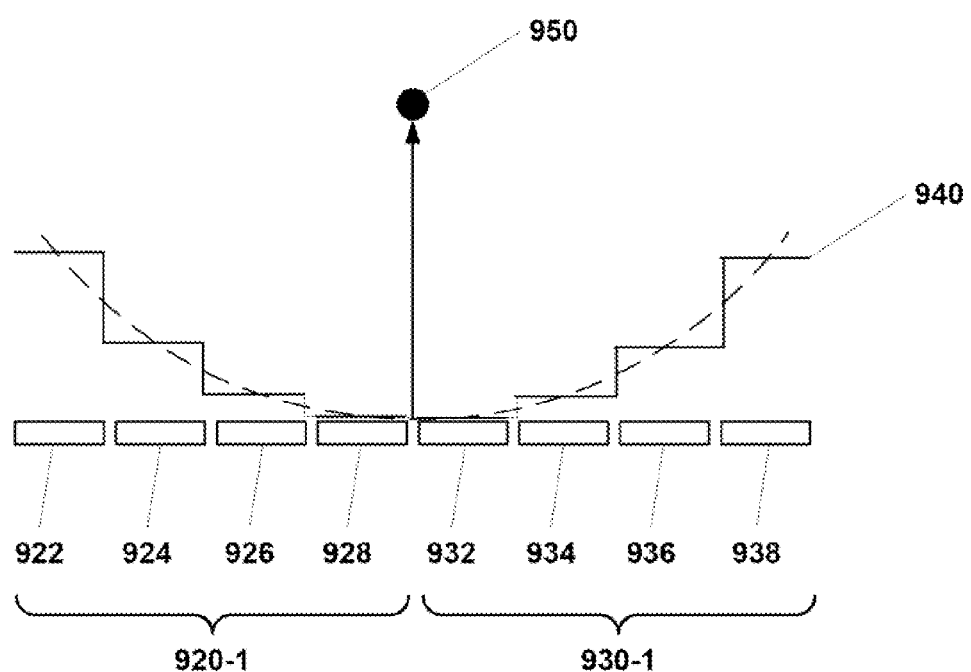
FIG. 20 is an illustration of synthetic aperture beamforming according to an embodiment of the invention.

Referring to FIG. 20, an ultrasound signal delay profile 940 for the eight element synthetic aperture imaging core 90 of FIG. 16 built from the two transducer array is illustrated. Ultrasound signals are first generated and detected by the four elements 922, 924, 926, 928 of the first transducer array 920. Ultrasound signals from the first transducer array 920 are stored on a computer-readable medium for subsequent analysis. Ultrasound signals are then generated and detected by the four elements 932, 934, 936, 938 of the second transducer array 930. Ultrasound signals from the second transducer array 930 are also stored on a computer-readable medium for subsequent analysis. The stored ultrasound signals from the first and second transducer arrays 920, 930 are then processed to focus the signals at a predetermined focal spot 950. The end-to-end positioning of the first and second transducer arrays 920, 930 is achieved by precise positioning of the imaging core by rapid linear translation and rotation. FIG. 20 illustrates focusing ultrasound signals in a direction perpendicular to the plane of the synthetic aperture.

Spatial compound imaging techniques may be used to reduce image artifacts due to temperature variations that occur during ablation procedures. Localized changes in the speed of sound due to heating or cooling of tissue by ablation catheters cause ultrasound image artifacts because standard beamformation algorithms assume a constant speed of sound. Spatial compound imaging techniques mitigate the thermoacoustic lens image artifacts by imaging tissue volumes of interest from multiple directions. Imaging directions comprising ultrasound propagation paths with fewer thermal variations generate fewer image artifacts.

Figure 21:
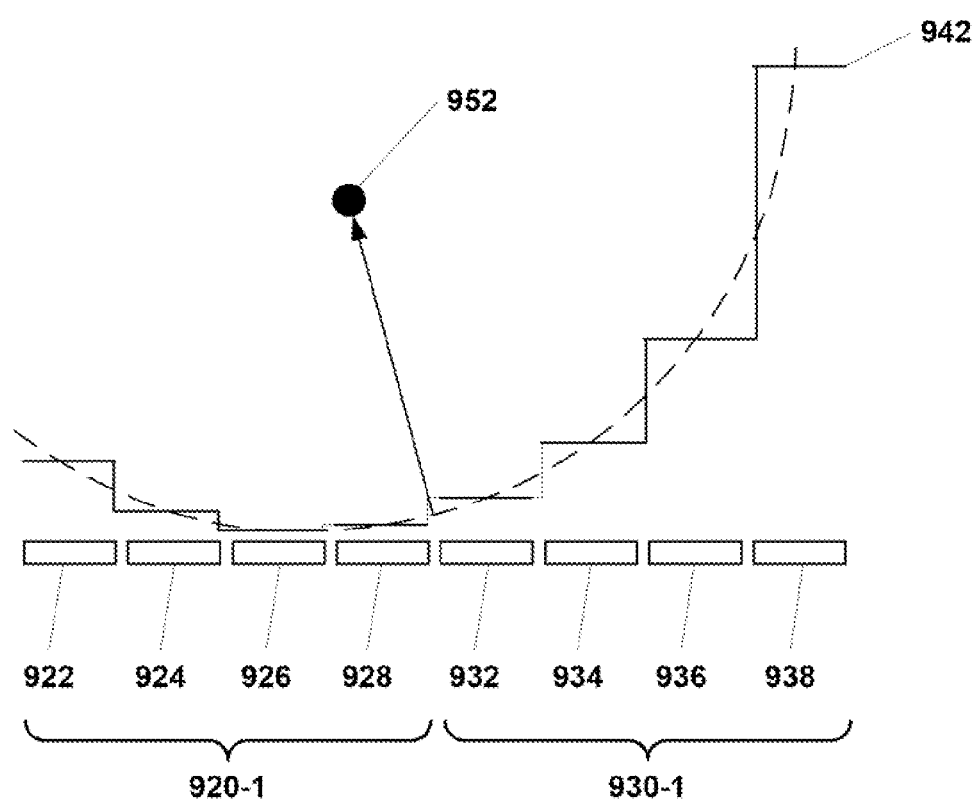
FIG. 21 is an illustration of synthetic aperture beam steering according to further aspects of the invention.

Referring now to FIG. 21, an ultrasound signal delay profile 942 for an eight element synthetic aperture, such as the imaging core 90 of FIG. 16, is used to steer ultrasound signals 20° off perpendicular to the face of the synthetic aperture. Ultrasound signals are first generated and detected by the four elements 922, 924, 926, 928 of the first transducer array 920. Ultrasound signals from the first transducer array 920 are stored on a computer-readable medium for subsequent analysis. Ultrasound signals are then generated and detected by the four elements 932, 934, 936, 938 of the second transducer array 930. Ultrasound signals from the second transducer array 930 are also stored on a computer-readable medium for subsequent analysis. The stored ultrasound signals from the first and second transducer arrays 920, 930 are then processed to focus the signals at a predetermined focal spot 952. The end-to-end positioning of the first and second transducer arrays 920, 930 is achieved by precise positioning of the imaging core by rapid linear translation and rotation. Spatial compounding combined with rapid linear translation and rotation of the imaging core enables a volume of interest to be insonified from multiple directions. An exemplary spatial compound imaging acquisition comprises five imaging directions −10°, −5°, 0°, +5°, and +10° from perpendicular to the face of the eight element synthetic aperture. The multiple images acquired at different imaging directions are then combined into a single spatial compound image. Spatial compound imaging techniques are known to those skilled in the art. The optimal number of spatial compound angles and aperture size for cardiac ablation monitoring is determined empirically.

Figure 22:
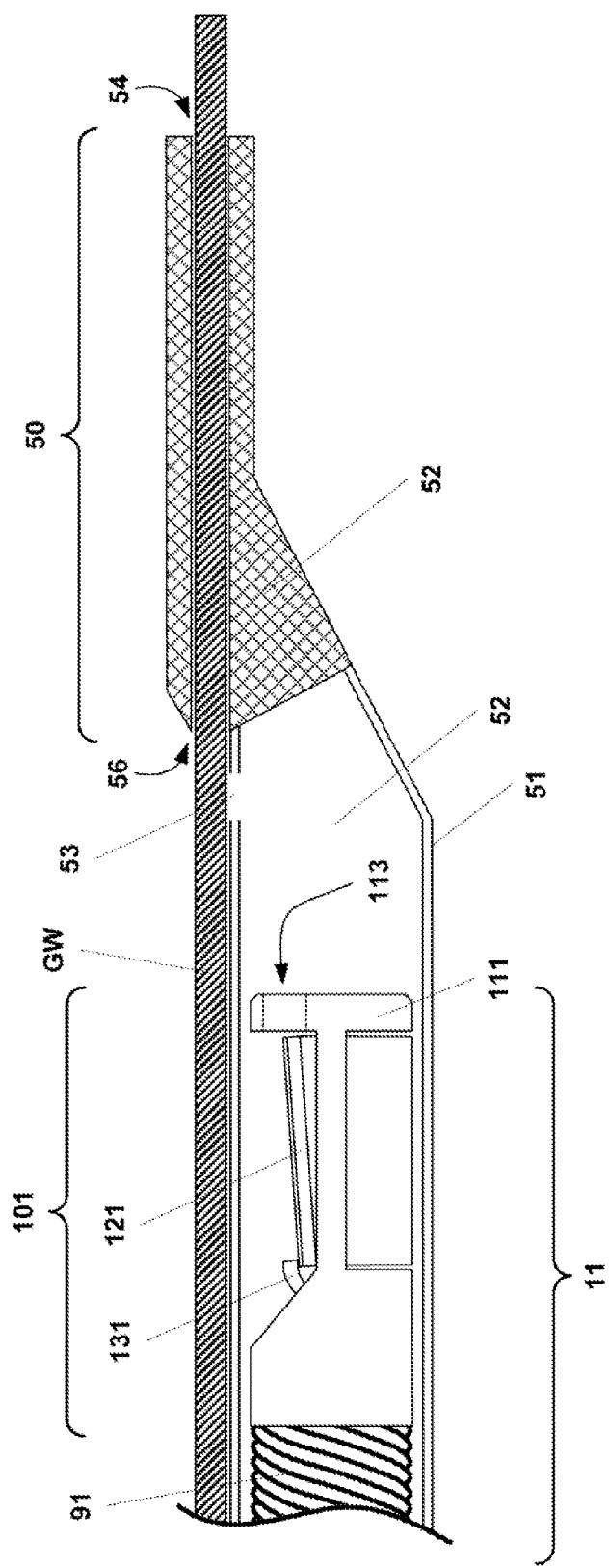
FIG. 22 is a side view in partial cross section of the distal section of a short monorail imaging catheter embodying the present invention.
Figure 23:
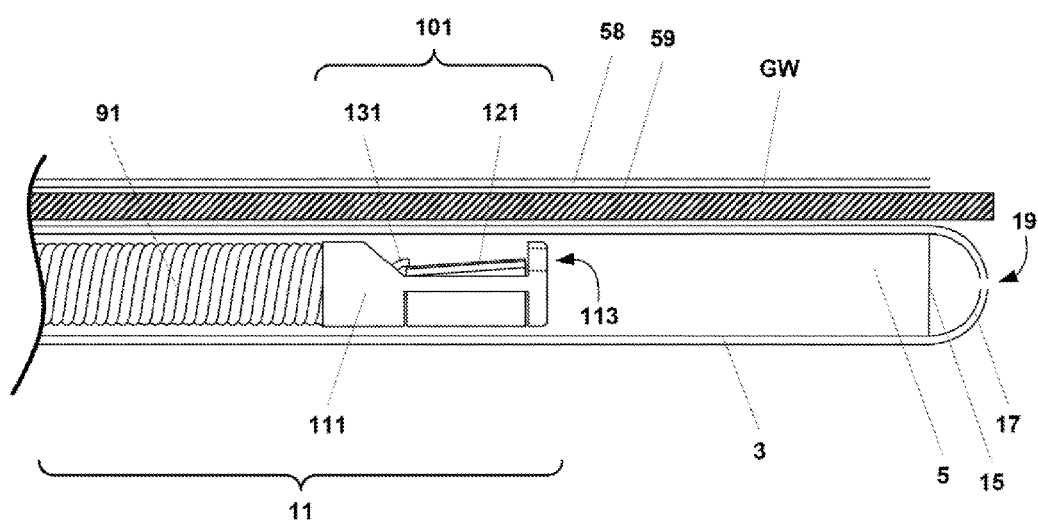
FIG. 23 is a side view of the distal section of a long monorail imaging catheter embodying aspects of the present invention.

Alternative catheter configurations can provide advantages for image guidance of AF ablation procedures. Referring now to FIGS. 22 and 23, alternative embodiments comprise a guidewire receiver lumen to facilitate delivery of the catheter to the anatomical site of interest.

FIG. 22 shows a distal section of an echocardiography catheter comprising a sheath 51, a distal tip 50, and an imaging core 11. The distal sheath 51 is bonded to the distal tip 50. The distal tip 50 is a short monorail (or rapid exchange) design adapted to receive a guidewire GW. The longitudinal axis of the distal tip 50 is substantially parallel to and offset from the longitudinal axis of the distal shaft 51. The imaging core 11 comprises a drive cable 91 attached to a distal housing assembly 101 wherein the distal housing assembly 101 comprises a distal housing 111, a transducer stack 121, and a transmission line 131. The distal housing 111 further comprises a distal opening 113 that facilitates fluid flow across the face of the transducer stack 121. The distal tip is described in U.S. patent application Ser. No. 12/547,972 which is hereby incorporated herein by reference.

FIG. 23 shows a distal section of an echocardiography catheter comprising a long monorail or over-the-wire design. The distal section comprises a distal shaft 3 having an imaging lumen 5 wherein an ultrasound imaging core 11 is positioned. The distal section further comprises a septum 15, an atraumatic distal tip 17, and a septum puncture port 19. The septum 15 may be comprised of a polymer material such as a room-temperature vulcanizing (RTV) silicone. A syringe needle (not shown) may be inserted through the septum puncture port 19 to puncture the septum 15 and fill the distal sheath lumen 5 with an ultrasonically transparent fluid such as a sterile saline solution. Upon withdrawal of the syringe needle the septum 15 seals itself. The use of a self-sealing septum prevents the pulling of fluids such as air into the distal sheath as the imaging core 11 translates towards the proximal end.

The imaging core 11 comprises a drive cable 91 attached to a distal housing assembly 101 wherein the distal housing assembly 101 comprises a distal housing 111, a transducer stack 121, and a transmission line 131. The distal housing 111 further comprises a distal opening 113 that facilitates fluid flow across the face of the transducer stack 121. The distal section still further comprises an additional lumen 59 adapted to receive a guidewire GW.

Figure 24:
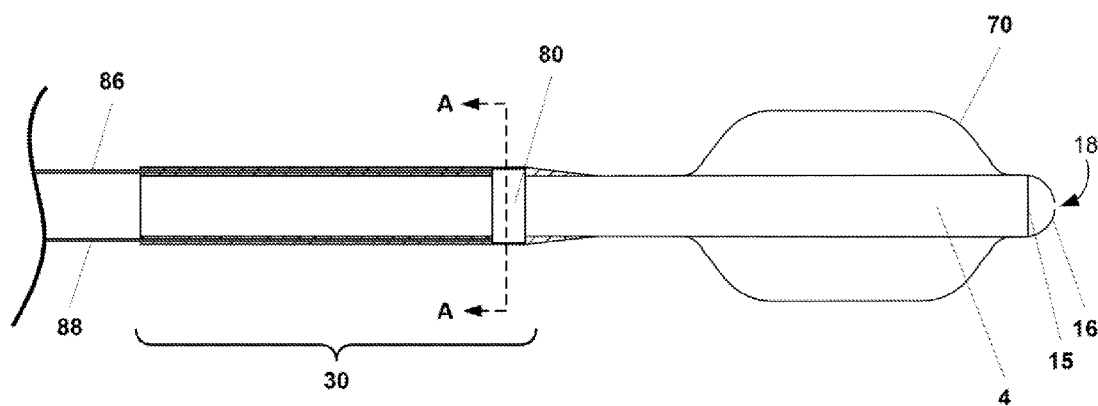
FIG. 24 is a side view of the distal section of a steerable imaging catheter according to aspects of the invention.
Figure 24A:
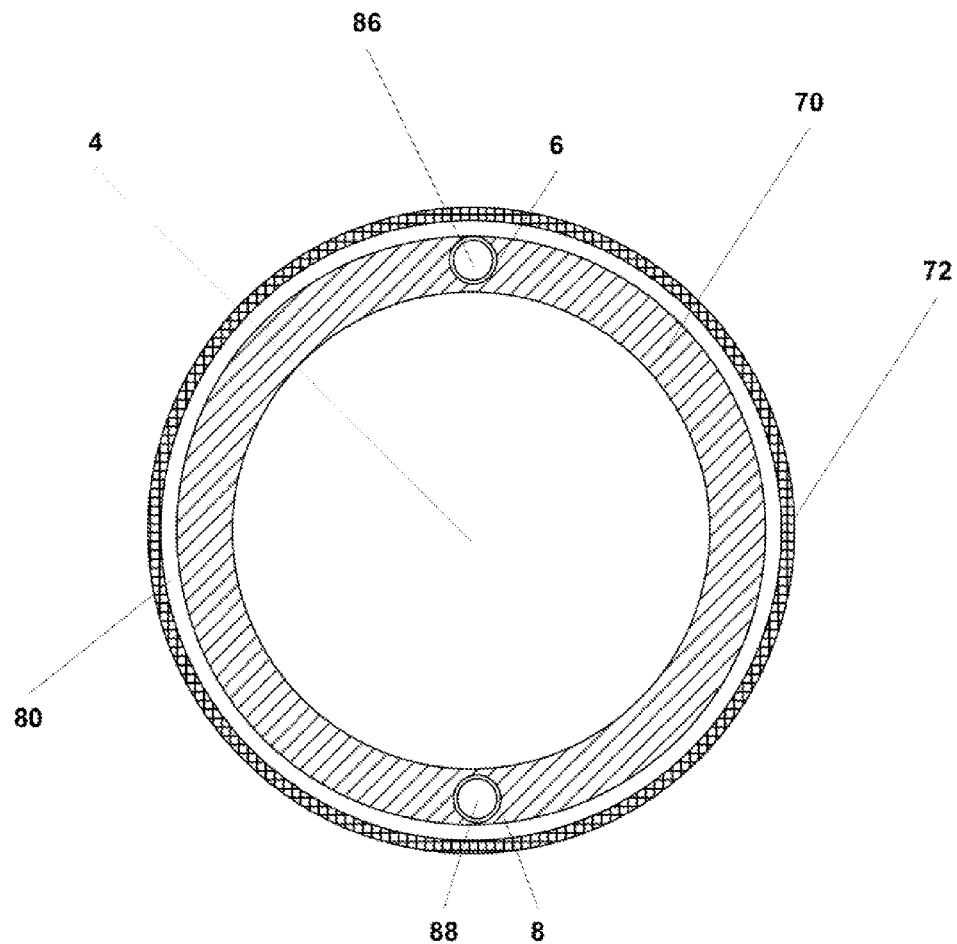
FIG. 24A is a sectional view taken along lines A-A of FIG. 24.

An alternative embodiment of an echocardiographic catheter comprises a steering capability. Referring now to FIG. 24, a distal section of a steerable catheter is shown. FIG. 24A shows a cross section cut of the catheter at a steering ring 80 of the steerable catheter. The steering ring 80 is embedded between a first and second thermoplastic layer 70, 72 in the steering segment 30 of the distal section of the catheter sheath. The steering section is generally proximal to the balloon and imaging window of the catheter. The steering ring may be laser cut from a stainless steel hypotube. The stainless steel steering cords 86, 88 extend from the proximal end of the catheter (not shown) to the steering ring 80 through steering cord lumens 6, 8. The steering cords are coupled to steering control mechanism (not shown) that enable steering of the catheter tip by the user. The steering cords are attached to the steering ring 80, generally by soldering, brazing, or laser welding. The steering segment 30 of the catheter is attached to a stiffer proximal section (not shown) that enables bending of the distal section of the catheter. The design and operation of steerable catheters are known to those skilled in the art.

Figure 25:
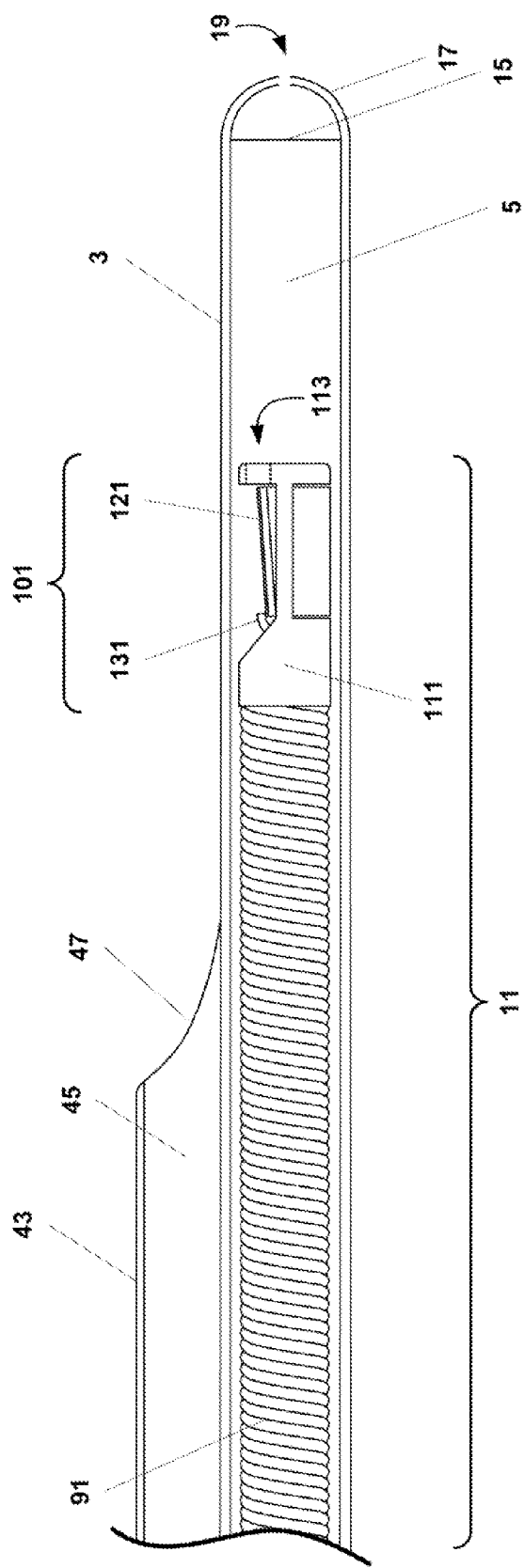
FIG. 25 is a side view in partial cross section of the distal section of an intracardiac echocardiography catheter embodying the present invention.

Referring now to FIG. 25, a side view of an embodiment of the distal section of an intracardiac echocardiographic catheter is shown. The distal section comprises an imaging core 11 and a working lumen 45. The working lumen 45 enables the use of additional devices such as electroanatomic mapping and ablation catheters. The exit port 47 of the working lumen is located proximal to the imaging window of the imaging lumen. The imaging core 11 comprises a drive cable 91 attached to a distal housing assembly 101 wherein the distal housing assembly 101 comprises a distal housing 111, a transducer stack 121, and a transmission line 131. The distal housing 111 further comprises a distal opening 113 that facilitates fluid flow across the face of the transducer stack 121. The distal section of the imaging catheter further comprises a sheath 3, a distal sheath lumen 5, a septum 15, an atraumatic distal tip 17, and a septum puncture port 19. The septum 15 is comprised of a polymer material such as a room-temperature vulcanizing (RTV) silicone. A syringe needle (not shown) is inserted through the septum puncture port 19 and punctures the septum 15 to fill the distal sheath lumen 5 with an ultrasonically transparent fluid such as a sterile saline solution. Upon withdrawal of the syringe needle the septum 15 seals itself. The use of a self-sealing septum prevents the pulling of fluids such as blood into the distal sheath as the imaging core 11 translates towards the proximal end.

The imaging catheter is sufficiently small, generally 8 Fr or smaller, such that the left atrium is accessed by a transseptal route. An intracardiac echocardiography catheter having an additional working lumen can potentially reduce the number of transseptal punctures required for image guidance of AF ablation procedures.

Figure 26:
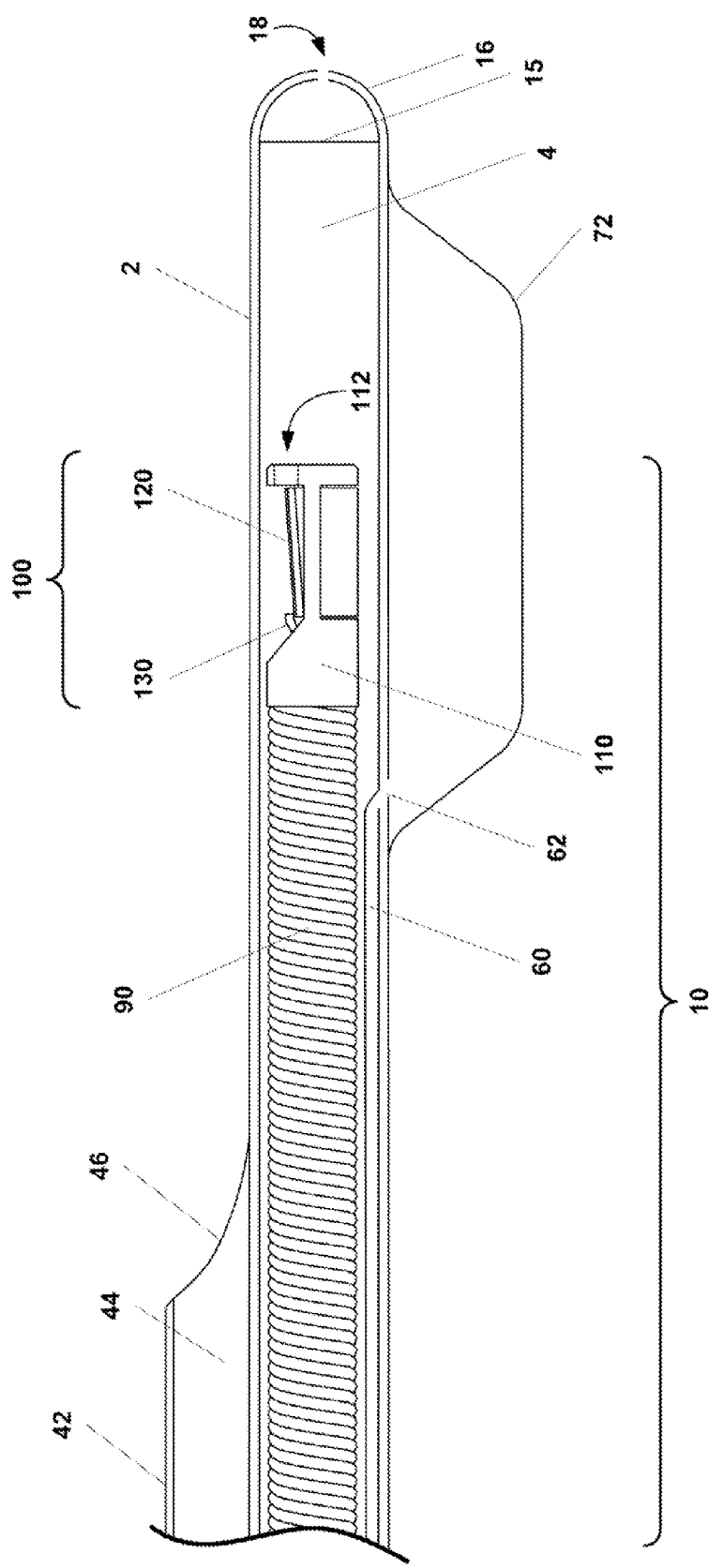
FIG. 26 is a side view in partial cross section of the distal section of a transesophageal echocardiography catheter embodying further aspects of the present invention.

Referring now to FIG. 26, a side view of another embodiment of the distal section of a transesophageal echocardiography catheter is shown. The distal section of the catheter comprises a balloon envelope 72, an ultrasonic imaging core 10, and a working lumen 44. The working lumen 44 enables the use of additional devices such as a steering stylet that may be useful for repositioning the esophagus relative to an ablation catheter during an ablation procedure. The ability to reposition the esophagus can potentially mitigate adverse events such as formation of atrio-esophageal fistula. The exit port 46 of the working lumen is located proximal to the imaging window of the imaging lumen. The ultrasonic imaging core 10 comprises a drive cable 90 and a distal housing assembly 100 further comprising a distal housing 110, a transducer stack 120, and a transmission line 130. The distal housing 110 further comprises a distal opening 112 that facilitates fluid flow across the face of the transducer stack. The transducer stack 120 can be focused or unfocused.

The distal section of the balloon imaging catheter further comprises a sheath 2, a distal sheath lumen 4, a septum 15, an atraumatic distal tip 16, and a septum puncture port 18. The septum 15 may be comprised of a polymer material such as a room-temperature vulcanizing (RTV) silicone. A syringe needle (not shown) may be inserted through the septum puncture port 18 to puncture the septum 15 and to fill the distal sheath lumen 4 with an ultrasonically transparent fluid such as a sterile saline solution. Upon withdrawal of the syringe needle the septum 15 seals itself. The use of a self-sealing septum prevents the pulling of fluids such as air into the distal sheath as the imaging core 10 translates towards the proximal end.

The distal sheath 2 is coupled to the esophageal wall by use of an ultrasonic couplant such as an ultrasonic gel couplant. The catheter is held in position relative to the esophageal wall by inflation of the balloon. The balloon expands typically to the side of the catheter distal from the heart. The balloon catheter is sufficiently small, generally 15 Fr or smaller, such that the esophagus may be accessed by a nasal route. The balloon envelope 72 is formed of a compliant polymer blend such as polyethylene/EVA and is attached, generally by bonding or fusing, to the distal catheter sheath section proximal and distal to an inflation port 62. The balloon assembly is 2 cm to 10 cm in length, generally 6 cm. The balloon envelope 72 is inflated using an ultrasonically transparent fluid, such as a sterile saline solution. The inflated balloon facilitates imaging of the esophageal wall and cardiac structures.

Figure 27:
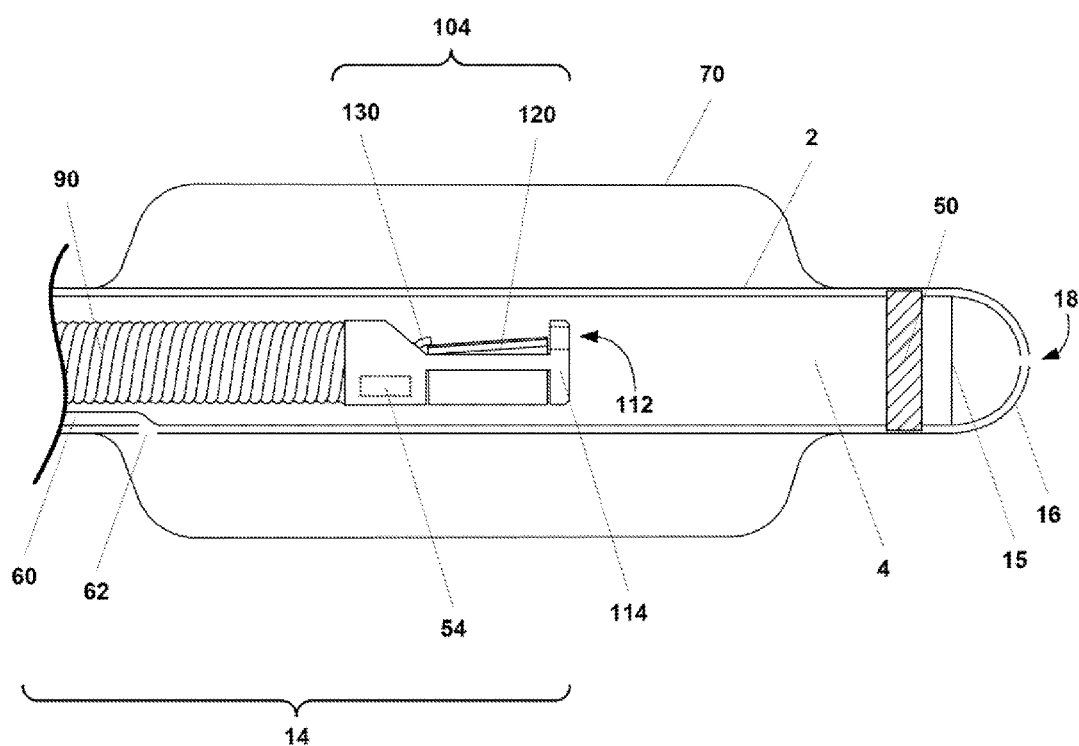
FIG. 27 is a side view in partial cross section of the distal section of another transesophageal echocardiography catheter embodying aspects of the present invention.

Referring now to FIG. 27, still another embodiment of a distal section of a transesophageal catheter is shown. The distal section comprises a balloon envelope 70, an inflation lumen 60, an inflation port 62, and an ultrasonic imaging core 14. The ultrasonic imaging core 14 comprises a drive cable 90 and a distal housing assembly 104 further comprising a distal housing 114, a transducer stack 120, and a transmission line 130. The distal housing 114 further comprises a distal opening 112 that facilitates fluid flow across the face of the transducer stack. The transducer stack 120 can be focused or unfocused. An exemplary transducer for a 15 Fr sized catheter has a circular aperture of up to approximately 4.2 mm and has a focal length between 1 cm and 4 cm, generally between 2 cm and 3 cm. Methods to focus transducers are known to those skilled in the art of transducer fabrication. The distal housing assembly 104 still further comprises a magnetic sensor 54. The magnetic sensor 54 comprises one, two, or three-axis coils with mutually orthogonal windings. The sensor detects AC or DC magnetic fields generated by an external transmitter (not shown). The sensor output enables tracking of the catheter imaging core by means of an external magnetic tracking system (not shown).

The distal section of the balloon imaging catheter further comprises a sheath 2, a distal sheath lumen 4, a septum 15, an atraumatic distal tip 16, a septum puncture port 18, and a radio-opaque marker band 50. The septum 15 may be comprised of a polymer material such as a room-temperature vulcanizing (RTV) silicone. A syringe needle (not shown) may be inserted through the septum puncture port 18 to puncture the septum 15 and to fill the distal sheath lumen 4 with an ultrasonically transparent fluid such as a sterile saline solution. Upon withdrawal of the syringe needle the septum 15 seals itself. The use of a self-sealing septum prevents the pulling of fluids such as air into the distal sheath as the imaging core 14 translates towards the proximal end.

The balloon catheter is sufficiently small, generally 15 Fr or smaller, such that the esophagus is accessed by a nasal route. The balloon envelope 70 is formed of a compliant polymer blend such as polyethylene/EVA and is bonded to the distal catheter sheath section proximal and distal to the inflation port 62. The balloon assembly is 2 cm to 10 cm in length, generally 6 cm. The balloon envelope 70 is inflated using an ultrasonically transparent fluid, such as a sterile saline solution. The balloon can be inflated up to 4 cm in diameter, generally between 2 cm and 3 cm. The inflated balloon facilitates imaging of the esophageal wall and cardiac structures. The radio-opaque marker band 50 is positioned distal to the balloon envelope 70. The radio-opaque marker band 50 enables catheter location under x-ray fluoroscopy.

While particular embodiments of the present invention have been shown and described, modifications may be made, and it is therefore intended to cover in the appended claims, all such changes and modifications which fall within the true spirit and scope of the invention as defined by those claims.

What is claimed:

1. A catheter-based imaging system comprising:
    a catheter having a telescoping proximal end, a distal end having a distal sheath and a distal lumen, a working lumen, and an ultrasonic imaging core, the ultrasonic imaging core being arranged for rotation and linear translation, the working lumen extending from the telescoping proximal end toward the distal end adjacent to the ultrasonic imaging core;
    a patient interface module (PIM) including a linkage arm mount, a rotational motor, a gear and arm system comprising a first gear coupled to a linkage arm, and an ultrasonic energy generator and receiver coupled to the ultrasonic imaging core, the rotational motor being directly coupled to the first gear, and the linkage arm being directly coupled to the linkage arm mount, wherein the rotational motor imparts controlled rotation to the ultrasonic imaging core and the rotational motor is adapted to drive the gear and arm system to impart controlled, linear, and bidirectional translation to the ultrasonic imaging core, wherein the PIM includes a translation stage, the translation stage being rigidly fixed to both the first gear and the rotational motor, and the linkage arm being adapted to couple the first gear to the linkage arm mount, and wherein the rotational motor imparts controlled linear, and bidirectional translation by rotating the first gear such that the translation stage is linearly translated relative to the linkage arm mount via the linage arm; and an imaging engine configured to electrically interface with the PIM, the imaging engine coupled to the ultrasonic energy receiver, the imaging engine adapted to generate an image.

2. The catheter-based imaging system of claim 1, wherein the catheter is adapted for intracardiac use.

3. The catheter-based imaging system of claim 1, wherein the catheter is adapted for transesophageal use.

4. The catheter-based imaging system of claim 1, further comprising a compliant balloon at the catheter distal end.

5. The catheter-based imaging system of claim 4, wherein the catheter comprises an inflation lumen in fluid communication with the balloon.

6. The catheter-based imaging system of claim 4, wherein the catheter comprises an inflation lumen and a deflation lumen in fluid communication with the balloon.

7. The catheter-based imaging system of claim 4, wherein the catheter distal end is in fluid communication with the balloon.

8. The catheter-based imaging system of claim 1, wherein the catheter is dimensioned for transnasal delivery.

9. The catheter-based imaging system of claim 1, wherein the ultrasonic imaging core comprises at least one transducer.

10. The catheter-based imaging system of claim 1, wherein the ultrasonic imaging core comprises at least one transducer array.

11. The catheter-based imaging system of claim 1, wherein the rotational motor comprises an ultrasonic piezoelectric motor.

12. The catheter-based imaging system of claim 1, wherein the PIM comprises a linear translation position sensor including a sensor array and a magnet disposed within the PIM, wherein linear translation of the ultrasonic imaging core causes a corresponding linear translation of the magnet relative to the sensor array, and wherein sensors of the sensor array are configured to sense the magnet and are aligned along a travel range of the magnet.

13. The catheter-based imaging system of claim 1, wherein the imaging engine is further adapted to identify susceptible substrates responsive to ultrasound tissue classifiers.

14. The catheter-based imaging system of claim 1, further comprising a temperature monitor that monitors luminal esophageal temperature responsive to ultrasound tissue classifiers.

15. The catheter-based imaging system of claim 9, wherein the imaging engine is further adapted to stitch scanned image sub-volumes into a large scanned image volume.

16. The catheter-based imaging system of claim 9, wherein the imaging engine is further adapted to be responsive to the ultrasonic imaging core to provide synthetic aperture imaging.

17. The catheter-based imaging system of claim 10, wherein the imaging engine is further adapted to be responsive to the at least one transducer array to provide synthetic aperture imaging.

18. The catheter-based imaging system of claim 9, wherein the imaging engine is further adapted to be responsive to the ultrasonic imaging core to provide synthetic aperture beam steering.

19. The catheter-based imaging system of claim 10, wherein the imaging engine is further adapted to be responsive to the at least one transducer array to provide synthetic aperture beam steering.

20. The catheter-based imaging system of claim 1, wherein the catheter distal end comprises a self-sealing septum, an atraumatic tip, and a septum puncture port.

21. The catheter-based imaging system of claim 1, wherein the catheter distal tip comprises a short monorail rapid exchange guidewire receiver.

22. The catheter-based imaging system of claim 1, wherein the catheter comprises an over-the-wire guidewire receiver.

23. The catheter-based imaging system of claim 1, wherein the catheter comprises a steerable section.

24. The catheter-based imaging system of claim 1, wherein the catheter comprises a second working lumen.

25. The catheter-based imaging system of claim 1, wherein the ultrasonic imaging core comprises a magnetic tracking sensor.

26. The catheter-based imaging system of claim 1, wherein the catheter distal sheath comprises a radio-opaque marker band.

27. A catheter-based imaging system, comprising:
a catheter having a telescoping proximal end, a distal end having a distal sheath and a distal lumen, a working lumen, and an ultrasonic imaging core, the ultrasonic imaging core being arranged for rotation and linear translation, the working lumen extending from the telescoping proximal end toward the distal end adjacent to the ultrasonic imaging core;
a patient interface module (PIM) including a linkage arm mount, a gear and arm system comprising a first gear coupled to a linkage arm, a rotational motor, a translation stage, and an ultrasonic energy generator and receiver coupled to the ultrasonic imaging core, linear rotational motor being directly coupled to the first gear, and the linkage arm being directly coupled to the linkage arm mount, wherein the rotational motor is adapted to impart controlled rotation to the ultrasonic imaging core and to drive the gear and arm system to impart controlled, linear, and bidirectional translation to the ultrasonic imaging core, and an ultrasonic energy generator and receiver coupled to the ultrasonic imaging core;
wherein the translation stage is rigidly fixed to the rotational motor, and wherein the rotational motor is configured to move along with and linearly translate the translation stage; and
an imaging engine configured to electrically interface with the PIM, the imaging engine coupled to the ultrasonic energy receiver, the imaging adapted to generate an image.

* * * * *